United States Patent
McErlean et al.

(10) Patent No.: US 7,010,899 B2
(45) Date of Patent: Mar. 14, 2006

(54) AUTOMATED PRESCRIPTION AND/OR LITERATURE BAGGER SYSTEM AND METHOD OPTIONALLY INTEGRATED WITH AUTOMATED DISPENSING SYSTEM AND/OR AUTOMATED LABELING AND PACKAGING SYSTEM

(75) Inventors: James G. McErlean, Allendale, NJ (US); Chih-Jen Leu, East Brunswick, NJ (US); Michael Joseph Szesko, Freehold, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

(21) Appl. No.: 10/634,991

(22) Filed: Aug. 6, 2003

(65) Prior Publication Data

US 2004/0123564 A1    Jul. 1, 2004

Related U.S. Application Data

(63) Continuation-in-part of application No. 10/215,249, filed on Aug. 9, 2002, now Pat. No. 6,892,512.

(60) Provisional application No. 60/401,340, filed on Aug. 7, 2002.

(51) Int. Cl.
  *B65B 61/26*    (2006.01)

(52) U.S. Cl. ............... 53/135.2; 53/135.1; 53/570; 53/459; 53/411

(58) Field of Classification Search .......... 53/570, 53/459, 415, 411, 385.1, 131.2, 131.4, 135.1, 53/135.2; 156/540, 541, 542
See application file for complete search history.

(56) References Cited

U.S. PATENT DOCUMENTS

| | | | |
|---|---|---|---|
| 3,653,176 A | | 4/1972 | Gess |
| 3,703,834 A | | 11/1972 | Beezer |
| 3,933,564 A | | 1/1976 | Jensen |
| 3,939,998 A | | 2/1976 | Soltermann |
| 4,351,679 A | | 9/1982 | Dreher |
| 4,363,685 A | | 12/1982 | White |
| 4,573,852 A | | 3/1986 | Rinfret et al. |
| 4,595,447 A | | 6/1986 | Lindstrom |
| 4,615,757 A | * | 10/1986 | Treiber ............ 156/350 |
| 4,647,333 A | | 3/1987 | Voltmer et al. |
| 4,668,327 A | | 5/1987 | Voltmer et al. |
| 4,705,588 A | * | 11/1987 | Treiber ............ 53/441 |
| 4,835,730 A | | 5/1989 | Shimano et al. |
| 4,944,647 A | | 7/1990 | Oleson et al. |
| 5,208,762 A | | 5/1993 | Charhut et al. |
| 5,298,104 A | * | 3/1994 | Absher ............ 156/363 |
| 5,370,754 A | * | 12/1994 | Soloman ............ 156/64 |
| 5,425,823 A | * | 6/1995 | Woodside, III ............ 156/64 |
| 5,468,110 A | * | 11/1995 | McDonald et al. ......... 414/273 |

(Continued)

FOREIGN PATENT DOCUMENTS

CA    2226379    1/1997

(Continued)

OTHER PUBLICATIONS

International Search Report for PCT/US03/24688 mailed Nov. 26, 2003.

(Continued)

*Primary Examiner*—Stephen F. Gerrity
*Assistant Examiner*—Hemant M. Desai
(74) *Attorney, Agent, or Firm*—Irah H. Donner; Wilmer Cutler Pickering Hale and Dorr LLP

(57) ABSTRACT

A system and method places a printed label on a bag. A first plurality of rollers can feed one or more bags, and a second plurality of rollers can feed one or more labels. A tamp pad can place the label on the bag.

53 Claims, 19 Drawing Sheets

U.S. PATENT DOCUMENTS

| | | | |
|---|---|---|---|
| 5,570,568 A * | 11/1996 | Kramer | 53/479 |
| 5,660,305 A | 8/1997 | Lasher et al. | |
| 5,713,485 A | 2/1998 | Liff et al. | |
| 5,761,877 A * | 6/1998 | Quandt | 53/155 |
| 5,771,657 A | 6/1998 | Lasher et al. | |
| 5,853,530 A * | 12/1998 | Allen | 156/541 |
| 5,865,918 A * | 2/1999 | Franklin et al. | 156/64 |
| 6,179,030 B1 * | 1/2001 | Rietheimer | 156/360 |
| 6,230,927 B1 | 5/2001 | Schoonen et al. | |
| 6,370,841 B1 | 4/2002 | Chudy et al. | |
| 6,413,345 B1 | 7/2002 | Treleaven | |
| RE37,829 E | 9/2002 | Charhut et al. | |
| 6,451,149 B1 * | 9/2002 | McKenney et al. | 156/238 |
| 6,470,648 B1 * | 10/2002 | Baker | 53/411 |
| 6,471,089 B1 | 10/2002 | Liff et al. | |
| 6,511,569 B1 | 1/2003 | Nixon et al. | |
| 6,543,201 B1 * | 4/2003 | Cronauer et al. | 53/131.5 |
| 6,580,968 B1 | 6/2003 | Yuyama et al. | |
| 6,688,346 B1 * | 2/2004 | Brahier et al. | 141/314 |
| 6,769,228 B1 * | 8/2004 | Mahar | 53/411 |
| 2001/0017817 A1 | 8/2001 | De La Huerga | |

FOREIGN PATENT DOCUMENTS

| | | |
|---|---|---|
| EP | 0292018 | 11/1988 |
| EP | 0 328 003 A1 | 8/1989 |
| EP | 0684130 | 11/1995 |
| EP | 0974524 | 1/2000 |
| EP | 1186285 | 3/2002 |
| GB | 990140 | 4/1965 |
| JP | 06315519 | 11/1994 |
| JP | 08052198 | 2/1996 |
| WO | 89/05727 | 6/1989 |
| WO | WO 99/17218 | 4/1999 |
| WO | 00349925 | 6/2000 |
| WO | WO 00/34925 | 6/2000 |

OTHER PUBLICATIONS

International Search Report PCT/US03/24685 mailed Dec. 2, 2003.

May 20, 2004. Written Opinion from PCT/US03/24685.

Apr. 30, 2004. International Preliminary Examination Report from PCT/US03/24688.

Jan. 29, 2004. International Search Report from PCT/US03/24686.

Jan. 28, 2004. International Search Report from PCT/US03/24687.

* cited by examiner

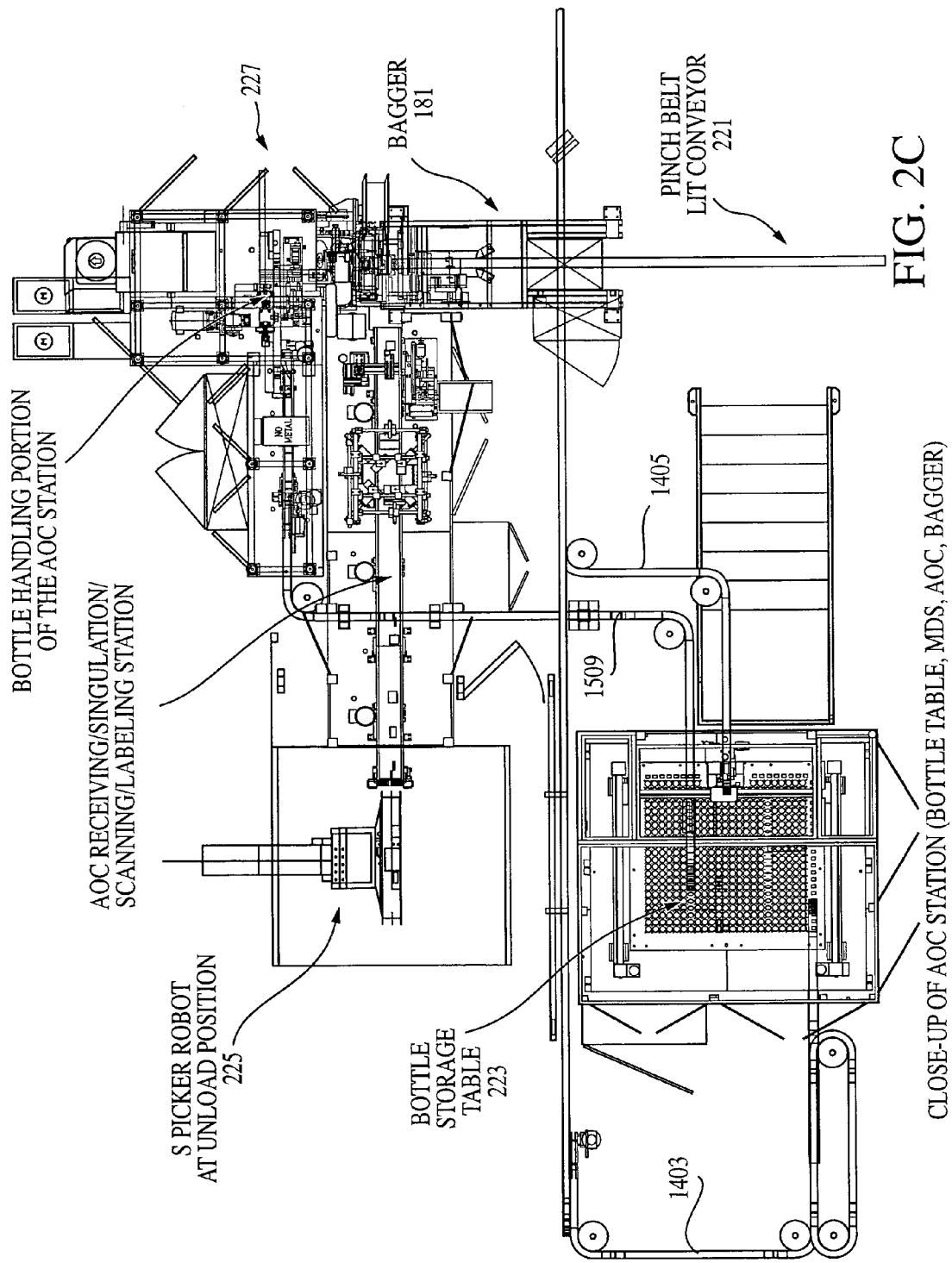

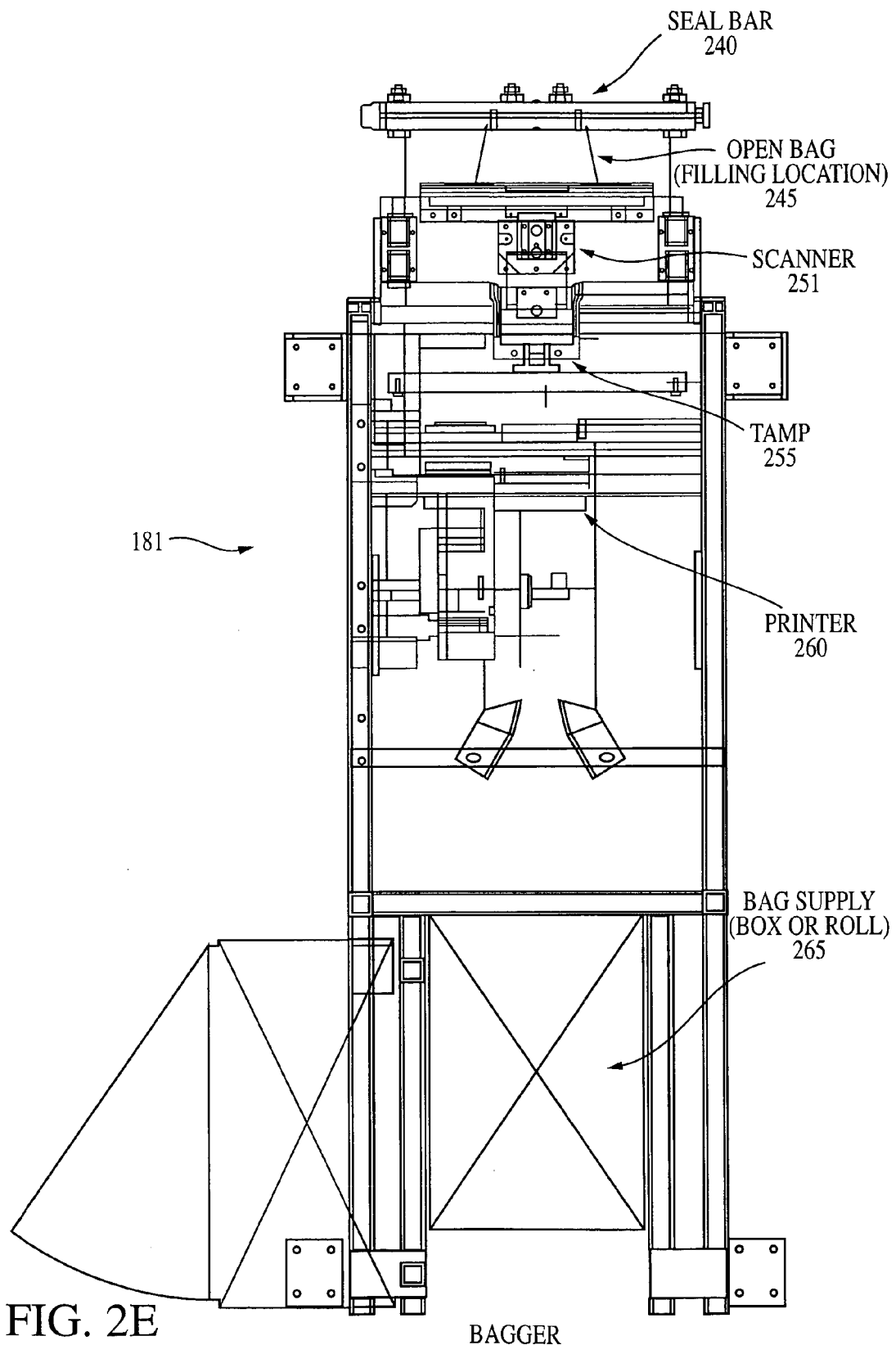
FIG. 2E  BAGGER

AUTOMATED PRESCRIPTION AND/OR LITERATURE BAGGER SYSTEM AND METHOD OPTIONALLY INTEGRATED WITH AUTOMATED DISPENSING SYSTEM AND/OR AUTOMATED LABELING AND PACKAGING SYSTEM

RELATED APPLICATIONS

This application claims priority to, and is a continuation-in-part of U.S. application Ser. No. 10/215,249, filed Aug. 9, 2002 now Pat. No. 6,892,512 issued on May 17, 2005, which claims priority from U.S. provisional application Ser. No. 60/401,340 filed Aug. 7, 2002, each incorporated herein by reference.

FIELD OF THE INVENTION

The present invention generally relates to systems and methods for placing one or more literature packages and/or one or more pharmaceutical containers, that include medications, into a container to facilitate delivery of the literature package(s) and/or pharmaceutical container(s) to a recipient.

BACKGROUND OF THE INVENTION

In mail service pharmacies and large retail pharmacies, prescription drugs are dispensed in a high volume. For such services, automatic pill dispensing systems can be used to dispense prescription drugs and label pill containers, which can then be provided to a patient for whom the prescription was written.

A known automatic pill dispensing system 100 is described in U.S. Pat. No. 5,771,657, which is incorporated herein by reference. In the patent, as shown in FIG. 1A, orders (e.g., orders to fill prescriptions) are received by a host computer 9 which forwards the orders to a distributed computer system that can include a central computer called Pharmacy Automation Controller 10 (PAC). PAC 10 maintains an order file of the information about each prescription to be filled that can include information needed to fill each prescription. The order file can, for example, be used to prepare a prescription label for each bottle/container (hereinafter bottle). The order file can also be used to facilitate printing literature that can be placed in a shipping container with the bottle(s). PAC 10 can also update the order file to maintain a record of the current status of each prescription being filled as it progresses through the automated system.

PAC 10 can control a set of Print, Apply and Load (PAL) stations 14 which print prescription bottle labels, apply the labels to bottles, and load the labeled bottles onto bottle carriers that preferably receive the bottles in scheduled locations. PAC 10 can also control a carrier conveyer system 21 that carries the bottle carriers to different parts of system 100, and one or more automatic drug dispensing machines 23 that dispense tablets and/or capsules into the bottles in the bottle carriers as they are carried by conveyer system 21. In addition, PAC 10 controls bottle cappers 25 that apply caps to the bottles, and OCP stations 29 that unload bottles from the carriers and place them in shipping containers corresponding to a patient order. Further, PAC 10 can control literature printers 31 which print literature, for each prescription order, that can be enclosed in an envelope. Finally, PAC 10 can utilize bar code data that identifies the prescription order. The bar code can show through a window in the envelope. Envelopes can be placed on a literature conveyer 34 which carries the envelopes from the literature printers 31 to the OCP stations 29.

Conveyer system 21 carries the bottles in the carriers from PAL stations 14 through the automatic drug dispensing machines 23 to bottle cappers 25, and then from bottle cappers to OCP stations 29. Conveyer system 21 also carries empty carriers back to PAL stations 14. From bottle cappers 25, conveyers 56 feed the carriers onto an endless conveyer loop 71 which transports, for example, four carriers of a rank to one of, say, six OCP stations 29. Other numbers of OCP stations 29 can also be utilized. OCP stations 29 each also have a literature dispensing mechanism, which inserts the printed literature into each shipping container with the filled and capped prescription bottles.

As shown in FIG. 1B, bottles to be automatically filled with the prescription drugs are introduced to the automated system by hoppers 37, which receive the bottles in bulk form and automatically feed the bottles to unscramblers 39. One of the hoppers 37 and one of the unscramblers 39 will be for large bottles (e.g., 160 cc), and the remaining hoppers and unscramblers will be for small bottles (e.g., 110 cc). The small bottle size can preferably accommodate a majority of the automatically filled prescriptions. In the unscramblers, the bottles are singulated and oriented so that the bottle opening first faces downward. The bottles are then righted and directed to PAL stations 14 on bottle conveyers 41 and 43, one for large bottles and one for small bottles.

Conveyers 45, under control by PAC 10, carry the bottle carriers from the four PAL stations 14 to carrier buffers at the entrances of the four automatic drug dispensing machines 23 in which the tablets or capsules of the prescriptions are automatically dispensed into the prescription bottles under the control of PAC 10. Because of the organization provided by the carriers, the bottles are arranged into four columns approaching each automatic dispensing machine 23. Since there are four automatic dispensing machines 23, 16 parallel prescription bottle columns can approach the dispensing machines. In this embodiment, the four automatic drug dispensing machines each have 384 drug dispensers arranged four columns wide and 96 rows deep to provide a total of 1,536 pill dispensers. The automatic drug dispensing machines are similar to those described in the U.S. Pat. No. 5,660,305, which is hereby incorporated by reference. Each dispensing lane is divided into 32 buffer assemblies, each containing twelve drug dispensers oriented six on each side of a conveyer within the dispensing machine.

The carrier will be released by PAL station 14 onto a conveyer 45 which carries the carrier loaded with the labeled empty prescription bottles to an automatic dispensing machine 23, of which there are four, one for each PAL station 14. When a carrier moves out of the last row position in a dispensing machine, all of the prescription bottles in that bottle carrier should be filled and a conveyer 56 transports the prescription bottles now filled with the prescriptions to a bottle capper 25.

Bottle quality assurance area 109 has several stations at which pharmacists can scan the bar code on the bottles and visually inspect the contents of the bottles. The scan of the bottle bar code will bring up a display on the pharmacist's terminal which preferably includes all the information regarding the particular prescription and order. Such information can include, for example, the drug name, and instructions which identify the reason for the verification. All of the bottles that pass this inspection can be inserted or reinserted by the pharmacist on a bottle stream conveyer 111 to send the inspected bottles to the BSP station 112. Conveyer 108 leads to a star wheel diverter mechanism 114 which, optionally under the control of a controller for BSP station 112, deposits the bottle in a bottle stream conveyer 116 leading to the bottle quality assurance area 109 or into a bottle stream conveyer 118 leading to BSP station 112.

If the literature pack is on conveyer 34, but because of failure of the bar code reader (not shown) or the literature sorting mechanism (not shown), does not get diverted at BSP station 112, conveyer 34 will carry the literature package to package quality assurance area 96 where the literature pack can be manually added to the package. If, because of a malfunction, a literature envelope is not deflected by a deflector 89 (FIG. 1C), because of, for example, an improper bar code on the envelope, the envelope will continue on conveyer 34 to the end of the conveyer and be dumped into a receptacle at the package quality assurance station 96. If the bag does not contain a literature pack, then the bag is diverted into a tote (not shown) which will then be transported by a conveyer 34 to the package quality assurance station 96, where the shipping container will be assembled with the literature pack manually 137.

As shown in the OCP station 29 of FIG. 1C, the four carriers of a rank are first received in a carrier buffer 75 from which they are loaded onto a turntable 77. An RFID tag reader (not shown) verifies that the correct carriers are in place on turntable 77, which selectively rotates the carriers into a position to have the bottles removed by robotic arm 79. OCP station 29 also contains equipment 91 for packing literature into shipping containers, which take the form of bags 83, along with the prescription bottles of a given order. OCP station 29 also includes a bagging machine 181 which presents the bags for successive orders to be loaded in sequence at a loading position. Bagging machine 181 can print a bar code identifying the order directly on each bag 83. The printed data may include the mailing address to which the shipping container is to be sent.

Bag 83 is shown at the loading position with its mouth open. The opening of the mouth of bag 83 can be accomplished by a blower (not shown) provided as part of bagging machine 181. Conveyer 34 brings envelopes 85 containing literature to be packed in shipping containers to OCP station 29 in the reverse sequence that the patient orders are to be packed at that OCP station 29 for a given rank of carriers. At OCP stations 29, literature conveyor 34 can be in the form of a literature sortation system of the type used in mail sortation by the U.S. Post Office. The literature sortation system can include a pair of belts 88 that pass the envelopes along from station to station. Deflector 89 can optionally be located between each pair of belts 88, and be controlled by the OCP station controller to deflect selected literature envelopes into a literature dispensing mechanism 91.

When a rank of carriers is directed to a given OCP station 29 by PAC 10 from bottle cappers 25, PAC 10 can send an unload message to the controller for the OCP station 29. The unload message can contain an indication of the sequence that the orders are to be unloaded from the rank of carriers at the station, as well as containing the information as to the scheduled position of the bottles of each order in the four carriers of the rank of carriers to be unloaded. At the same time that PAC 10 sends an unload message to the controller of the OCP station 29, it can send a corresponding autopublish message to printers 31. The message can contain the information to be printed for the complete orders contained in the rank of carriers being sent to an OCP station 29. The autopublish message will also contain the sequence in which the corresponding orders are to be unloaded at the OCP station 29. In response to the autopublish message, one of the printers 31 will print literature for the orders and deposit the literature packs for the orders on literature conveyer 34 in reverse order from that in which the orders are to be unloaded at the OCP station 29.

Each literature pack is preferably enclosed in an envelope having a die cut window through which a bar code is readable by a bar code reader 87. The bar code can be printed by an appropriate printer 31 to identify the order for which the literature pack is printed. As the envelopes containing literature packs are carried past the OCP station 29 in the literature sortation system, the bar code readable through the window in each envelope will be read by a bar code reader 87, that can verify that the bar code coincides with an order in the unload message received by the controller for OCP station 29. The controller for OCP station 29 will then cause deflector 89 to deflect the envelope into literature dispensing mechanism 91. Since the conveyor brings the literature envelopes to an OCP station 29 in the reverse sequence that the corresponding patient order is to be packed at the packing station, the envelopes will be packed into the dispensing mechanism in that sequence. When bag 83 is ready to be packed at an OCP station 29, literature dispensing mechanism 91 first inserts a literature envelope into the bag 83 where it will be positioned at one side of the bag (by, e.g., gravity). This effect is achieved by orienting the bag 83 at a slight tilted position at bagging machine 181. After the literature has been inserted, robotic arm 79 unloads the bottles of the order from the scheduled positions in the four carriers on the turntable in accordance with the unload message. Robotic arm 79 preferably includes a bar code reader so that each time a bottle is lifted out of a carrier by robotic arm 79, the label on the bottle is read and verified.

The prescription bottles are then loaded into the bag 83 by a bottle loading mechanism 93. When the shipping containers 83 have been verified and filled with a literature pack and with a patient's order, the bag is sealed and dropped onto a conveyer 95 which carries the sealed shipping container to a mailing area where the bag is read and logged and then mailed to the customer. If the bag 83 does not contain a literature pack, then the bag is diverted into a tote 99 which will then be transported by a conveyer 101 to the package quality assurance station 96 where the shipping container will be assembled with the literature pack manually.

SUMMARY OF THE INVENTION

The present invention provides additional information and features with regard to the bagging machine disclosed, for example, in FIG. 1C. The bagging machine disclosed herein can also be advantageously used in connection with other pharmaceutical dispensing systems, as will be described herein.

The present invention includes a system that places a label on a bag. The system includes a first plurality of rollers contacting a bag film that includes a plurality of bags, each bag being delimited by a perforation. The first plurality of rollers define an area through which the bag film is conveyed, and rotate in concert in a first direction to convey the bag film. At least one of the plurality of rollers is driven to convey the bag film. The system also includes a printer for printing a plurality of labels disposed on a backing material.

The system also includes a second plurality of rollers that contact the plurality of labels and the backing material. The second plurality of rollers can define an area through which the plurality of labels and the backing material are conveyed. The second plurality of rollers rotate in concert to convey the plurality of labels and the backing material for indicia to be printed thereon. The system also includes a tamp that receives at least one printed label and places the printed label on the bag.

At least one of the second plurality of rollers can be under a biasing force, and move dynamically as labels are received by said printer. A spring can be used to provide the biasing force. In addition, a cam can be used that moves in concert with the at least one of the second plurality of rollers under the biasing force. The cam can engage a switch, such that when one of the second plurality of rollers includes a label roll, labels are dispensed from the label roll when the switch is engaged by the cam.

The system can also include a first sensor for determining a first position of the bag. The tamp can place the printed label on the bag responsive to the first position determined by the first sensor.

In addition, the system can also include at least one bag opening mechanism movably mounted to open the bag subsequent to labeling. A seal bar assembly can also be provided that includes a heater element and a seal bar to seal the bag. The seal bar can move toward the bag to seal the bag.

The at least one bag opening mechanism can include a second sensor to determine whether the bag is in position for opening. The first plurality of rollers can also rotate in a second direction subsequent to sealing the bag to break a perforation between the bag and a second bag.

A third sensor can be provided that detects a position of a perforation between the bag and a second bag. The perforation position can be used to convey the bag a predetermined amount in the first direction to the seal bar assembly.

In addition, a third roller can be provided that separates at least one of the plurality of labels from the backing material when the backing material rotates about the third roller. A surface of the tamp can include a plurality of vacuum holes that facilitate maintaining the label on the surface prior to placing the printed label on the bag.

While a first bag can be tamped, a second bag can substantially simultaneously be opened by the at least one bag opening mechanism. A motor and a belt can also be utilized to drive the at least one of the first plurality of rollers.

The system can also include a controller that associates at least one of a pharmaceutical container and a literature package corresponding to a prescription order with the bag label. A robotic mechanism can be used to place the pharmaceutical container in the bag.

A system in accordance with an embodiment of the present invention can also include a first dancer assembly that receives and conveys a bag film the includes a plurality of bags, each bag being separated by a perforation. The first dancer assembly can define an area through which the bags are conveyed, and can include a plurality of rollers. A motor and belt can drive at least one of the plurality of rollers. The system can also include a printer for printing a plurality of labels disposed on a backing material.

A second dancer assembly can convey the plurality of labels and the backing material, and define an area through which the plurality of labels and the backing material are conveyed. A tamp can receive at least one printed label.

A control system can associate at least one of a pharmaceutical container and a literature package corresponding to a prescription order with the label. A sensor system can be provided that senses a first position of the bag with respect to the tamp to facilitate the tamp placing the printed label on the bag, responsive to the first position determined by the sensor system.

The system can also include at least one bag opening mechanism movably mounted to open the bag subsequent to labeling, and a seal bar assembly that includes a heater element and a seal bar to seal the bag. The at least one bag opening mechanism can include a first sensor to determine whether a bag is in position for opening.

A second sensor can also be utilized that detects a position of a perforation between the bag and a second bag. The perforation position can be used to convey the bag a predetermined amount in a first direction to the seal bar assembly. The seal bar can move toward the bag to seal the bag. At least a portion of said first dancer assembly can rotate in a second direction subsequent to sealing the bag to break a perforation between the bag and a second bag.

A roller can be used that separates at least one of the labels from the backing material when the backing material rotates about the roller. A surface of the tamp can include a plurality of vacuum holes that facilitate maintaining the label on the surface prior to placing the printed label on the bag.

The second dancer assembly can include a roller under a biasing force that moves dynamically as labels are received by the printer. A spring can provide the biasing force. In addition, a cam can be provided that moves in concert with the roller under the biasing force.

The system can also include a switch that is engaged by the cam, and a label roll so that when the switch is engaged by the cam, labels are dispensed from the label roll. The label roll can be a part of the second dancer assembly.

A method for filling a plurality of prescription orders in accordance with an embodiment of the present invention can include the steps of transporting in a first direction a bag film that includes a plurality of bags, and transporting in the first direction a plurality of labels disposed on a backing sheet. The name and address information of a recipient of a prescription order can be printed on a label for each of the plurality of bags. The label can be placed on one of the plurality of bags from the bag film, when the corresponding bag reaches a predetermined position. The labeled bags can be opened, a pharmaceutical container with enclosed pharmaceuticals, corresponding to a prescription order associated with the bag label, can be placed in the opened bag. A literature pack corresponding to a prescription order can also be placed in the opened bag. A method in accordance with the present invention can also include the step of discarding a bag that cannot be opened.

The opened bag can also be sealed. The bag can be conveyed a predetermined amount in the first direction to a position where the bag is opened, responsive to detecting a perforation between two bags. A sensor can optionally be used to verify that a bag is in position for opening. Optionally after sealing, the bag can be transported in a second direction subsequent to break a perforation between the bag and a second bag.

Labels can be separated from the backing sheet prior to placing a label on a bag. A vacuum can be used to hold the label in place prior to placing the label on the bag. A label can be placed on a first bag substantially simultaneously while opening a second bag that already has a label placed thereon.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

The various features of novelty which characterize the invention are pointed out with particularity in the claims annexed to and forming a part of this disclosure. For a better understanding of the invention, its operating advantages and the specific objects attained by its uses, reference should be made to the accompanying drawings and descriptive matter in which there is illustrated preferred embodiments of the invention.

NOTATIONS AND NOMENCLATURE

The detailed descriptions which follow may be presented in terms of program procedures executed on computing or processing systems such as, for example, a stand-alone computing machine, a computer or network of computers. These procedural descriptions and representations are the means used by those skilled in the art to most effectively convey the substance of their work to others skilled in the art.

A procedure is here, and generally, conceived to be a sequence of steps leading to a desired result. These steps are those that may require physical manipulations of physical quantities (e.g., combining various pharmaceutical products into packages). Usually, though not necessarily, these quantities take the form of electrical, optical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices, including, but not limited to, microprocessors.

BRIEF DESCRIPTION OF THE DRAWINGS

The detailed description of the present application showing various distinctive features may be best understood when the detailed description is read in reference to the appended drawing in which:

FIGS. 2A–2E are exemplary diagrams illustrating aspects of an automated pill dispensing system that can utilize the bagger system disclosed herein;

DETAILED DESCRIPTION OF THE INVENTION

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Embodiments of the present invention are directed to dispensing orders that include various pharmaceutical products (e.g., bottles that contain counted pills, packages that include liquid or pre-packaged pharmaceutical products and/or patient specific literatures). In embodiments of the present invention, the term "pills" also refer to tablets, capsules and other similar terms known in the art. As used herein, the term pill can thus be used interchangeably with, for example, the terms tablet and/or capsule.

Figure 2A:
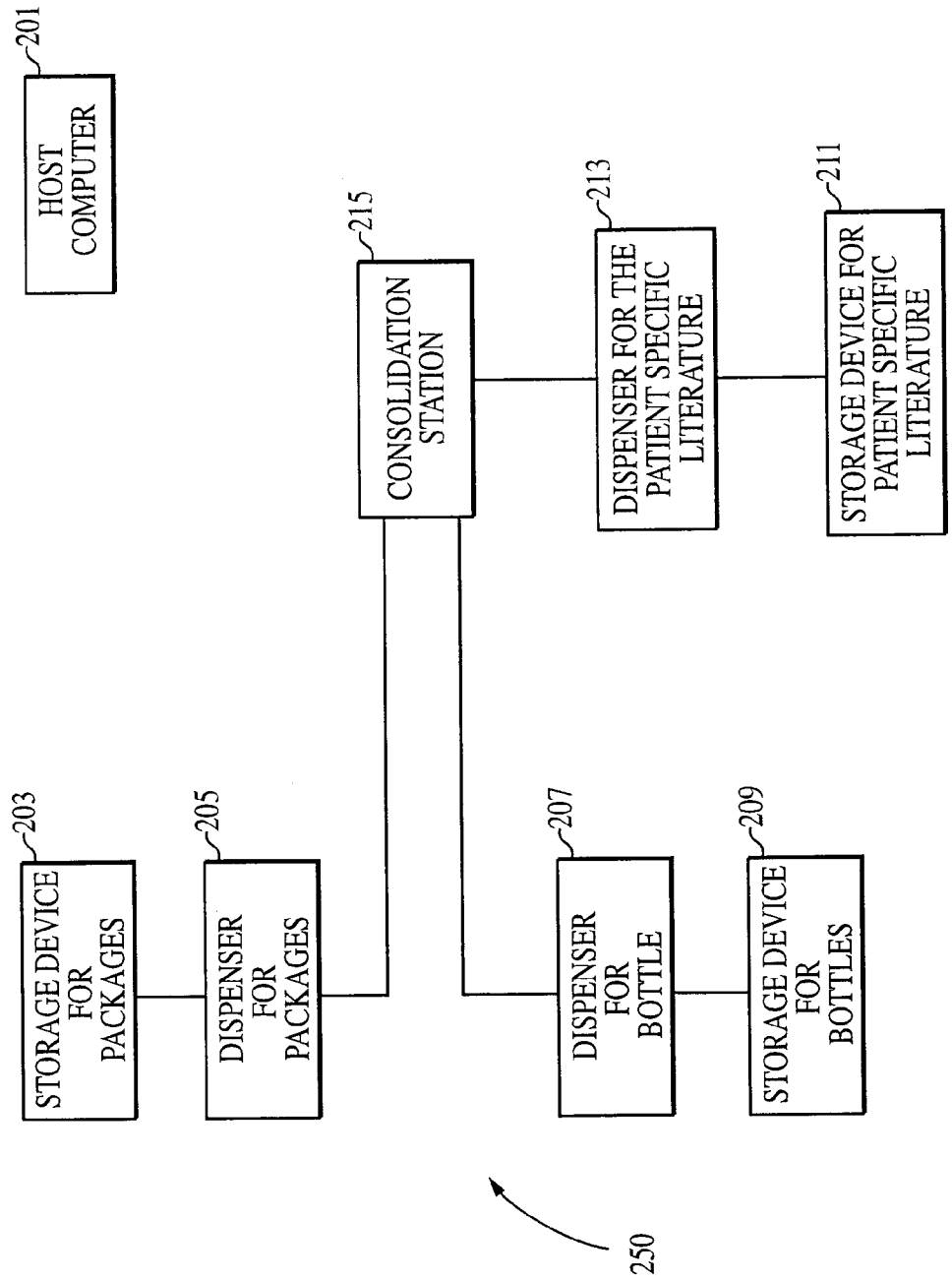

FIGS. 2A–2E show the automated prescription filling system with automated labeling and packaging 250 as described in U.S. patent application Ser. No. 10/215,249, which is incorporated herein by reference. System 250 can be referred to as a automated labeling and packaging system (ALPS). In particular, FIG. 2A shows a system 250 that can include a storage device for packages 203, a dispenser for the packages 205, a storage device for bottles filled with counted pills 209, a dispenser for the bottles with counted pills 207, a storage device for patient specific literatures 211, a dispenser for the patient specific literatures 213, a consolidation station 215, and a host computer 201.

The system shown in FIGS. 2A–2E can also include one or more local computers (not shown). For instance, each of the components (e.g., 203, 205, 209, 207, 211 and 213) can be connected to one or more local computers. The local computers in turn are optionally connected to central or host computer 201. In this way, the optional central or host computer 201 and local computers can be configured to control the various components of the present invention.

A local computer can also function with a standard Programmable Logic Controller (PLC). A PLC typically includes an I/O card to turn on/off a device. Accordingly, when a component is to be controlled by turning it on/off, a PLC can be used. When a large quantity of data is to be exchanged, a local computer can be used.

Central computer 201 can receive a request to fill an order, optionally in combination with the local computer(s) and/or the various components. Alternatively, local computers can receive the request to fill an order directly. In response, host computer 201 creates an order number and determines whether the order contains an order that requires bottles to be filled by counting individual tablets, and whether the order contains an order that requires packages from the storage device for bottles 209.

The storage device for packages 203 stores packages that contain pharmaceutical products. For example, one set of packages may contain a predetermined number of tablets (e.g., 500 tablets) of a certain drug (e.g., Allegra). Another set of example packages may include liquid pharmaceutical products. The packages can be made by original producers of drugs (e.g., Hoechst Marion Roussel). The packages can also be bulk bottles that are filled by any one of many automated (e.g., the ADDS) or manual methods known in the art. These packages can then be shelved so that their locations can be automatically identified. In turn, the dispenser for the packages 205 is configured to automatically identify the location of any package with a certain type of drug, dosage and/or quantity and configured to pick one or more packages from the identified location. In other words, a package contains a pharmaceutical product without having been pre-designated for any specific order when the package was created.

In operation, the command to locate and pick one or more packages is received from host computer 201. The dispenser for packages can also be connected to its own local computer to perform the necessary functions to locate and pick one or more packages in accordance with the command from host computer 201. Packages stored in the storage device for packages 203 are not designated for any specific patient. In other words, any package can be picked to fill an order of a patient as long as the type of drug, dosage and/or quantity are matched with the order.

FIG. 2A can also include a standard sensor or a standard counter to indicate when a specific type of package is out of stock in the storage device for packages 203. These sensors or counters can be present at each location (or a substantial number of them). The signals from the sensors or counters can be communicated to, for example, the central or host computer 201 via the local computer. In turn, central or host computer 201 can notify an operator or system to replenish the specific packages and/or stop the process of filling orders that require the specific type of package that are out of stock in the storage device for packages 203. In addition, or optionally, central or host computer 201 can send a query to the storage device for packages 203 regarding whether a certain number of certain packages are available to be dispensed. In response, the storage device for packages 203, or in combination with its local computer, can send a response based on information from the sensors and/or counters. Alternatively, sensors may be placed on a picking device (e.g., a robot arm) to provide the similar functionality. In yet another alternative, sensors are not utilized and the system keeps logical control by knowing how many packages have been placed in a channel and how many packages have been removed from the channel.

The dispenser for bottles 207 is configured to receive bottles that contain specific number (e.g., 1–500 or more) of pills for a specific order. For example, one bottle may include 350 tablets of one type of drug for patient A, while another bottle may include 600 tablets of another type of drug for patient B. The bottles can be filled by any automatic dispensing mechanisms known in the art (e.g., the system shown in U.S. Pat. No. 5,771,657, which is incorporated herein by reference). Bottles can also be manually filled (by, e.g., a pharmacist).

If an automatic dispensing system is used, central or host computer 201 sends commands to fill bottles with certain number of pills for a certain type of drug. Once they are filled, the bottles are stored in the storage device for bottles 209. In a similar fashion, in a manual system, the dispensing person would receive an instruction to count certain number of tablets for a certain type of drug. The person fills bottles according to the instructions and forwards the bottles to the storage device for bottles 209.

Once the storage device for bottles 209 receives all the bottles necessary to fill an order, the storage device for bottles 209 or in connection with its local computer sends a message to, for example, the central or host computer 201 indicating that the bottle portion of the order has been filled. For example, an order to be filled may require 1450 pills of a certain type of drug. In this example, the storage device for packages 203 may already have two packages each with 500 pills of the drug. If so, one bottle with 450 pills of the drug is necessary to fill the bottle portion of the order. (If one bottle cannot receive all 450 pills then more than one bottle would become necessary to provide the 450 pills).

The storage device for literature packs 211 contains literature to be packaged with specific orders. For example, a set of literature packs for one order may include information relating to each of the prescribed drugs, how often each drug must be taken, billing information, special instructions from the prescribing doctor, insurance information, refilling information and/or general information, for example health or notification of other services. The set of literature packs is then packaged per order and collected in the storage device for literature packs 211. Once the necessary literature packs are created, the storage device for literature packs 211, or in combination with its local computer, can notify the host computer 201 that the literature pack has been printed.

Upon receiving various information from the storage device for packages 203, storage device for bottles 209 and storage device for literature packs 211, computer 201 then sends instructions to the dispenser for the packages 205, dispenser for bottles 207 and dispenser for literature packs 213, or to their local computers, to dispense necessary bottle(s), package(s) and literature pack(s) to fill one or more orders. The dispensed bottle(s), package(s) and literature pack(s) are then consolidated by the consolidation station 215 and then sent, distributed or mailed out directly or indirectly to patients associated with the orders.

Figure 2B:
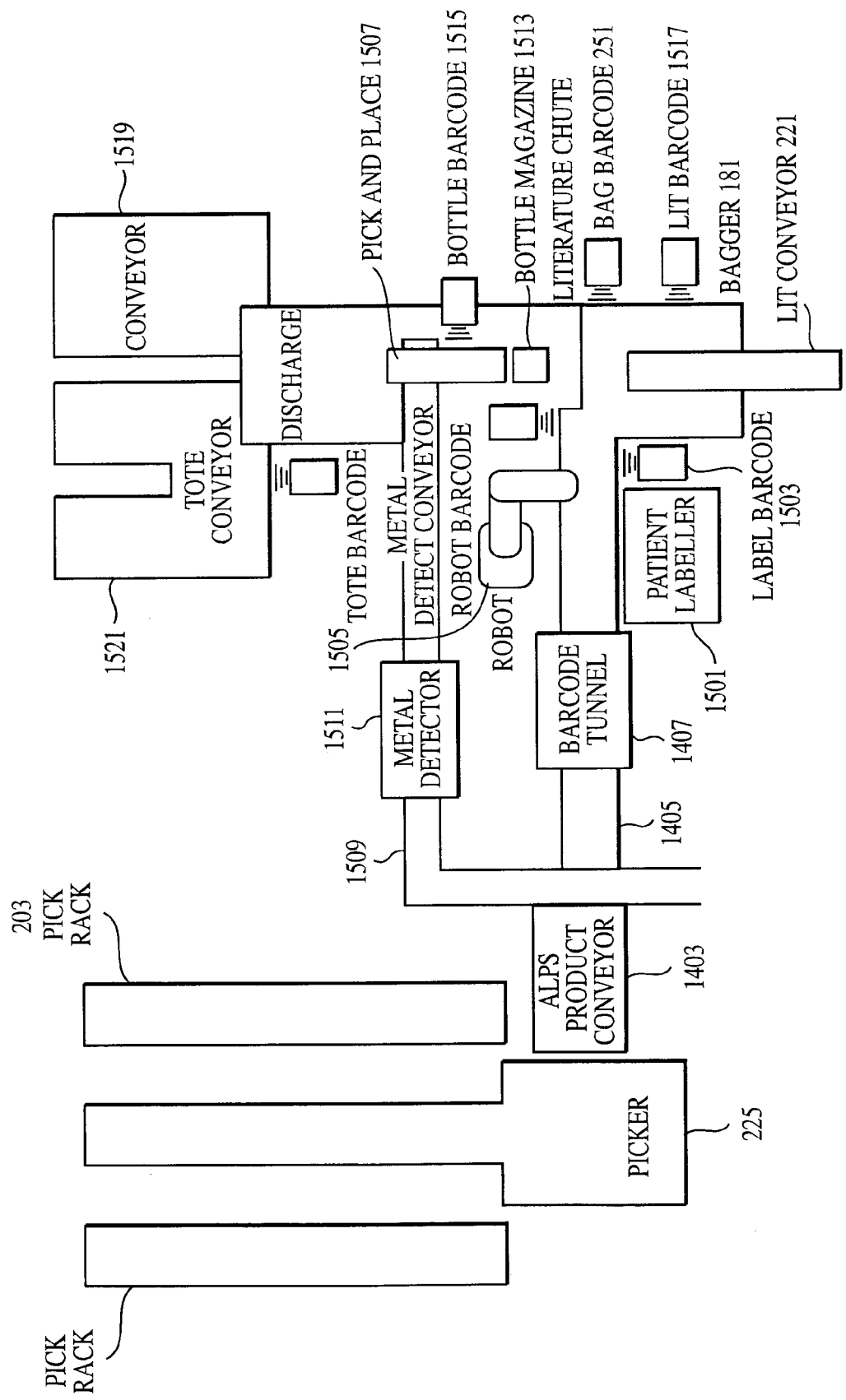

FIG. 2B shows an exemplary block diagram of aspects of system 250. Picking robot 225 can pick pharmaceutical containers from pick racks 203. Induct belt 1403 is configured to receive packages picked and unloaded by the picking robot 225. Received packages are then transported to a separation and accumulation belt 1405 configured to put gaps between the packages. The separation and accumulation belt 1405 then moves the packages into a set of barcode scanners in barcode tunnel 1407. Tunnel 1407 scanners are configured to detect and read barcodes from, for example, any of five exposed sides of the packages. (Since the packages are boxes, when the packages are placed on the belt 1405, five sides are exposed other than the side that touches the belt.) In such embodiments, when the packages are replenished into the shelves, their barcodes should preferably not be on the bottom. In some other embodiments, only a top side can be scanned as long as the packages are placed into the shelves so that their barcodes are on the top. Accordingly, any combination of barcode readers can be used as long as barcodes on the packages can be detected and read. It should be noted that in some embodiments of the present invention, belt 1405 can be transparent so that barcodes from the bottom side of the packages can also be detected and read by a barcode reader located below the belt 1405.

When barcodes are read, they can be verified by a local computer, which ensures that the scanned package actually belongs to the order that is about to be filled by the consolidation station 215. After the barcode scanners are used, the images of the packages are captured by a camera (not shown). The images are then sent to the local computer to determine the shape and orientation of the packages as they lay on belt 1405. Based on the determined shape, height and orientation, the local computer commands robot 1505 arm to pick up the package from belt 1405. An example of conventional computer vision software includes Adept AIM System, Motionware, Robot & Vision, Version 3.3B-Jun. 9, 1999, U.S. Pat. No. 4,835,730, incorporated herein by reference.

The local computer causes a patient label to be printed by the patient labeler 1501 for each package. While a package is picked up by the robot 1505 and being transported, its label is affixed to the package. Then robot 1505 can move the package next to the barcode reader 1503. The presence of a correct label is determined by the label barcode reader 1503. In addition, robot 1501, label barcode reader 1503, and their local computer can also be configured to cooperate with each other to detect labels and reject any packages without a label or with an incorrect label. Once, the package is determined to have a correct label affixed thereto, robot 1505 can drop the package into the bag opened in (and by) bagger 181.

With respect to bottles, metal detect conveyor 1509 can have a metal detector 1511 which can determine the presence of metallic substances in the bottles. Bottles with metallic substances can be rejected. The bottles belonging to one order are then placed into a standard bottle magazine 1513 by a standard pick-and-place device 1507 (e.g., a robot). An example of pick-and-place devices includes Stelron, Model: SVIP-A-M-P-6.00, X-2.00 Y-spec, U.S. Pat. No. 3,703,834, Mahwah, N.J. In this example embodiment, bottle barcode reader 1525 is provided to ensure that correct bottles have been delivered to the bottle magazine. Once all the bottles have been loaded to the bottle magazine, they can be released into a corresponding bag 83 held (and opened) by bagger 181.

With respect to the literature packs, they are transported to bagger 181 via literature conveyor 221. As the packs arrive at bagger 181, their barcodes are detected and checked by literature barcode reader 1517 to verify that correct literature packs are to be included in the bag 83. As the literature packs arrive, they are discharged into bag 83 as will be discussed herein.

In an embodiment, conveyor belt 221 can have three positions. Position 1 designates the position on the belt 221 in which its literature pack is ready to be disposed into the bag 83 at bagger 813. Position 2 designates the position on the belt 221 in which its literature pack can be discarded if some error is detected. Position 3 designates the position on the belt 221 in which a barcode reader 1517 can detect and read the barcode of the literature pack.

Literature handling logic can report on the status of the literature packs in the three positions. Consolidation logic can instruct literature handling logic to perform one or more tasks (e.g., accept or reject certain literature packs and/or advance the conveyor belt 221).

With regard to bagger 181, bags 83 are fed from the bag supply 265 (FIG. 2E), for example, one at a time. As bags 83 move up through bagger 181, a label or information about the order that is about to be filled is placed on the bag 83. For example, standard tamp 255 (FIGS. 4A and 5) can be used to place the label on a bag 83. The label or information is then detected and read by a scanner or barcode reader 251, which can verify that the correct label is printed and/or the label is properly affixed to the bag 83. As will be discussed herein, bagger 181 can then open bag 83 to place one or more literature packages and/or pharmaceuticals therein.

If bagger 181 seals a bag 83, the sealed bag 83 can be placed on a conveyor belt 1519 for subsequent distribution to a patient. If bagger 181 leaves a bag unsealed, the unsealed bags can be placed in a tote, which is placed on tote conveyor 1521. The tote is then transferred to an operator who can then completely fill the order by manually adding any (additional) required package(s).

FIG. 2C is a top view of a schematic illustrating an exemplary consolidation station, as is shown in block diagram for in FIG. 2B. In particular, FIG. 2B illustrates the bottle storage table 223 for the bottles, picking robot 225 and conveyor belt 221 for the literature packs. The bottles, packages and literature packs are combined in the order consolidation station 227, and put into one or more bags 83 at the bagger 181.

In operation, bottles filled with counted pills are stored at bottle storage table 223. When a complete set of bottles is received by the bottle storage table 223, its local computer notifies computer 201 that all the bottles for a particular order have been received. In response, computer 201 causes literature packs for the order to be printed and sent to the dispatch unit (either in a batch or individually). When the literature packs are received, they are organized such that literature packs for one order are next to each other. A dispatch unit (not shown) can determine the sequence of orders that the literature packs are received by reading identification codes affixed (or printed) on the literature packs. The dispatch unit then sends the literature packs, as they are received and sequenced, to the order consolidation station 227 via the conveyor belt 221. The dispatch unit can also notify the computer 201 the sequence of literature packs.

Upon receiving the information from the dispatch unit, computer 201 can instruct the bottle storage table 223 to release corresponding bottles, and picking robot 225 to pick corresponding packages of the order. The example embodiment is further configured such that the bottles, packages and literature packs all arrive at bagger 181 simultaneously for each order, although bagger 181 can optionally receive them at different times in storage locations for later bagging. This configuration allows bagger 181 to put the bottles, packages, and literature packs into one or more bags automatically. In alternative embodiments, computer 201 may be more involved or less involved based upon specific filling programs, volume, etc.

Figure 2D:
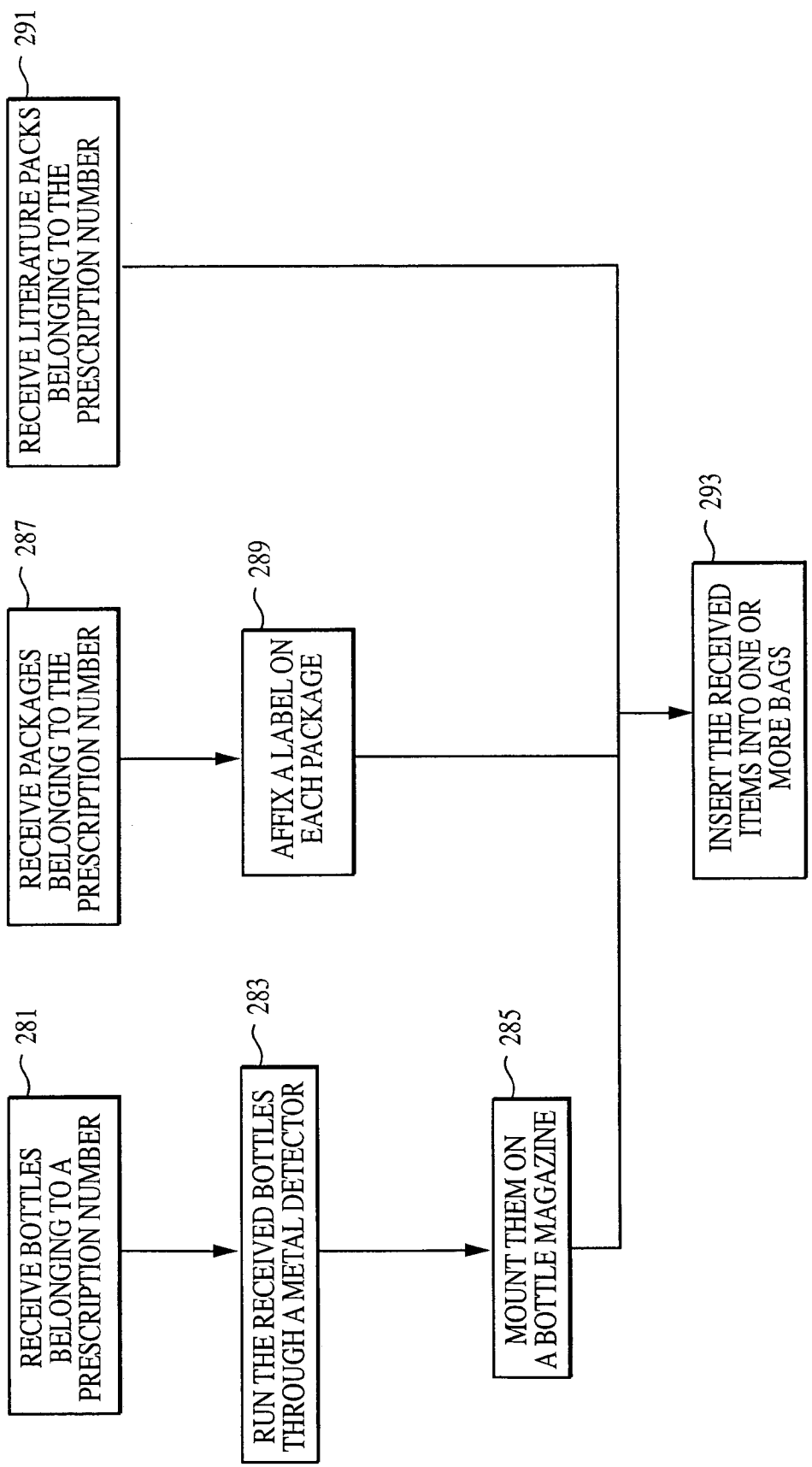

FIG. 2D illustrates the steps taken by the various components, their local computers, and computer 201 in the order consolidation station 215. In particular, bottles belonging to one order number are received from bottle storage table 223 (step 281). The received bottles are run through the metal detector 1511 (step 283). The bottles are then mounted on bottle magazine 1513 by pick-and-place device 1507 (step 285). Simultaneously, packages belonging to the same order number are received from storage device for packages 203 (step 287). A label is affixed to each of the received packages (step 289). Again simultaneously or substantially simultaneously, conveyor belt 221 moves literature packs belonging to the same order number to bagger 181. When all the items arrive, they are disposed into one or more bags 83 at the bagger 813.

If any error is detected, the items belonging to the same order number are all sent to a quality assurance station. If the error cannot be resolved, the order is cancelled and re-ordered or re-assembled. Host computer 201 reinitiates the process from the beginning to fill the order again. The example errors can be a rejected bottle because a metallic substance was detected, a patient label not being affixed to a package, and/or incorrect literature packs being delivered, etc.

FIG. 2E is diagram illustrating an exemplary high level view of bagger 181, which includes a supply of bags 265, a printer 260, tamp 255, a scanner 251, a mechanism 245 to open a bag and hold it open and a seal bar assembly 240 to seal the bag. In operation, bags are fed from the bag supply 265. As the bags move up through the bagger 181, a label or information about the order that is about to be filled is placed on bag 83. For example, the label may be printed and then pressed against the bag by the tamp 255. The label or information is then detected and read by scanner 251, which can determine whether the correct label is printed and/or the label is properly affixed to bag 83. Bag 83 is then opened to receive one or more prescriptions and optionally one or more corresponding literature packages.

If bag 83 contains all the items necessary to fill the order, then the bag 83 is sealed. Optionally, bag 83 is not sealed, if an error is detected. If one or more manually picked packages are required, then bag 83 is left unsealed.

Figure 3A:
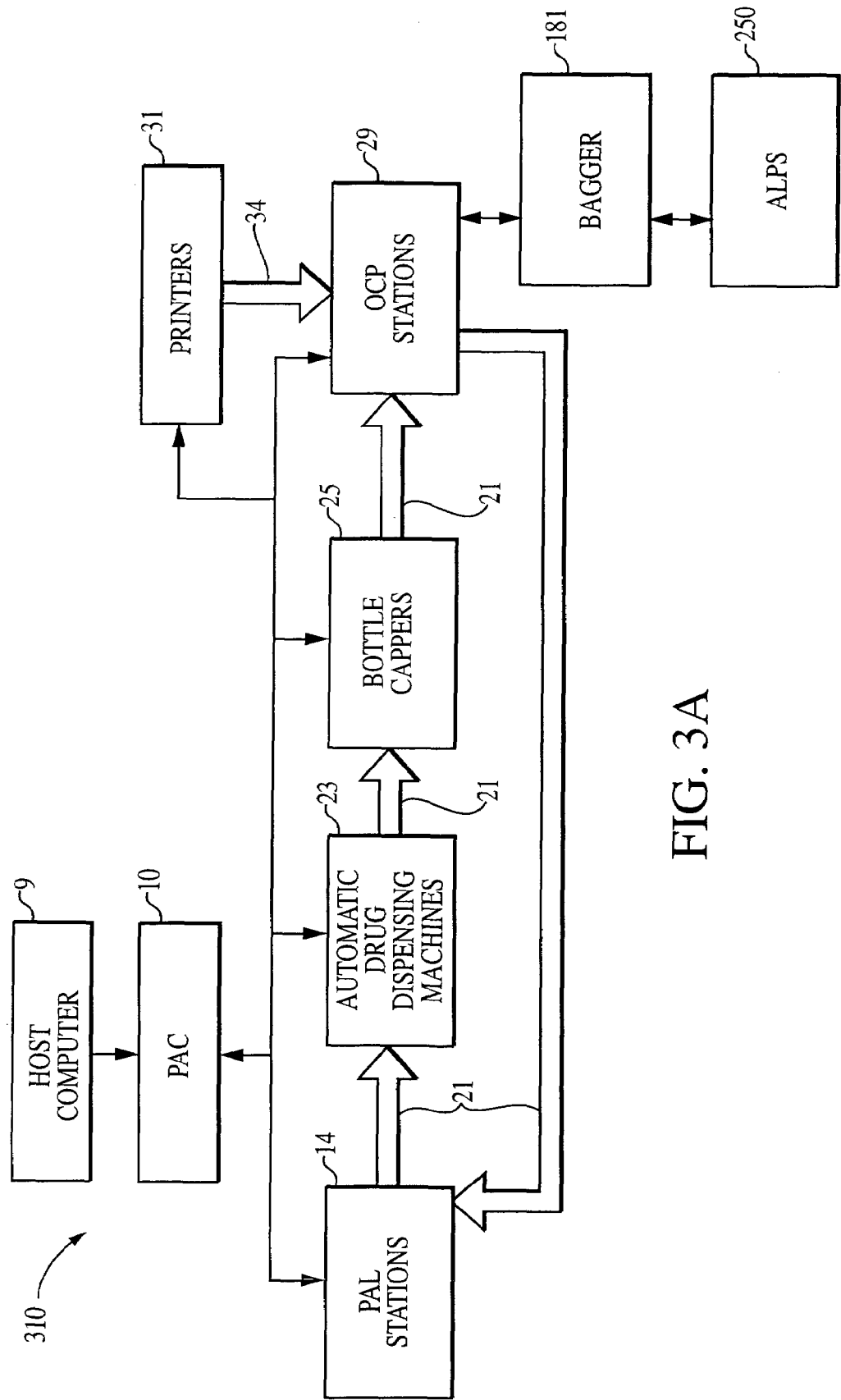
FIG. 3A is an exemplary diagram illustrating an embodiment of an automated pill dispensing system in accordance with the present invention.

FIG. 3A is an exemplary diagram illustrating an automated pill dispensing system 310 in accordance with an embodiment of the present invention. In operation, orders (e.g., orders to fill prescriptions) are received by a host computer 9 which forwards the orders to a distributed computer system that can include, for example, any standard computer such as a central computer called Pharmacy Automation Controller 10 (PAC). PAC 10 maintains an order file of the information about each prescription to be filled that can include information needed to fill each prescription. The order file can, for example, be used to prepare a prescription label for each bottle/container (hereinafter bottle). The order file can also be used to facilitate printing literature that can be placed in a shipping container with the bottle(s). PAC 10 can also update the order file to maintain a record of the current status of each prescription being filled as it progresses through the automated system.

PAC 10 can control a set of Print, Apply and Load (PAL) stations 14 which print prescription bottle labels, apply the labels to bottles, and load the labeled bottles onto bottle carriers that preferably receive the bottles in schedules locations. PAC 10 can also control a carrier conveyer system 21 that carries the bottle carriers to different parts of system 100, and automatic drug dispensing machines 23 that dispense tablets and/or capsules into the bottles in the bottle carriers as they are carried by conveyer system 21. In addition, PAC 10 controls bottle cappers 25 that apply caps to the bottles, and OCP stations 29 that unload bottles from the carriers and place them in shipping containers corresponding to a patient order. Further, PAC 10 can control literature printers 31 which print literature, for each prescription order, that can be enclosed in an envelope. Finally, PAC 10 can utilize a bar code that identifies the prescription order. The bar code can show through a window in the envelope. Envelopes can be placed on a literature conveyer 34 which carries the envelopes from the literature printers 31 to the OCP stations 29.

Conveyer system 21 carries the bottles in the carriers from PAL stations 14 through the automatic drug dispensing machines 23 to bottle cappers 25, and then from bottle cappers to OCP stations 29. Alternative sequences may optionally be used. Conveyer system 21 also carries empty carriers back to PAL stations 14. From bottle cappers 25, conveyers 56 feed the carriers onto an endless conveyer loop 71 which transports, for example, four carriers of a rank to one of, say, six OCP stations 29. Other numbers of OCP stations 29 can also be utilized. OCP stations 29 each also have a literature dispensing mechanism, which inserts the printed literature into each shipping container with the filled and capped prescription bottles.

Figure 1A:
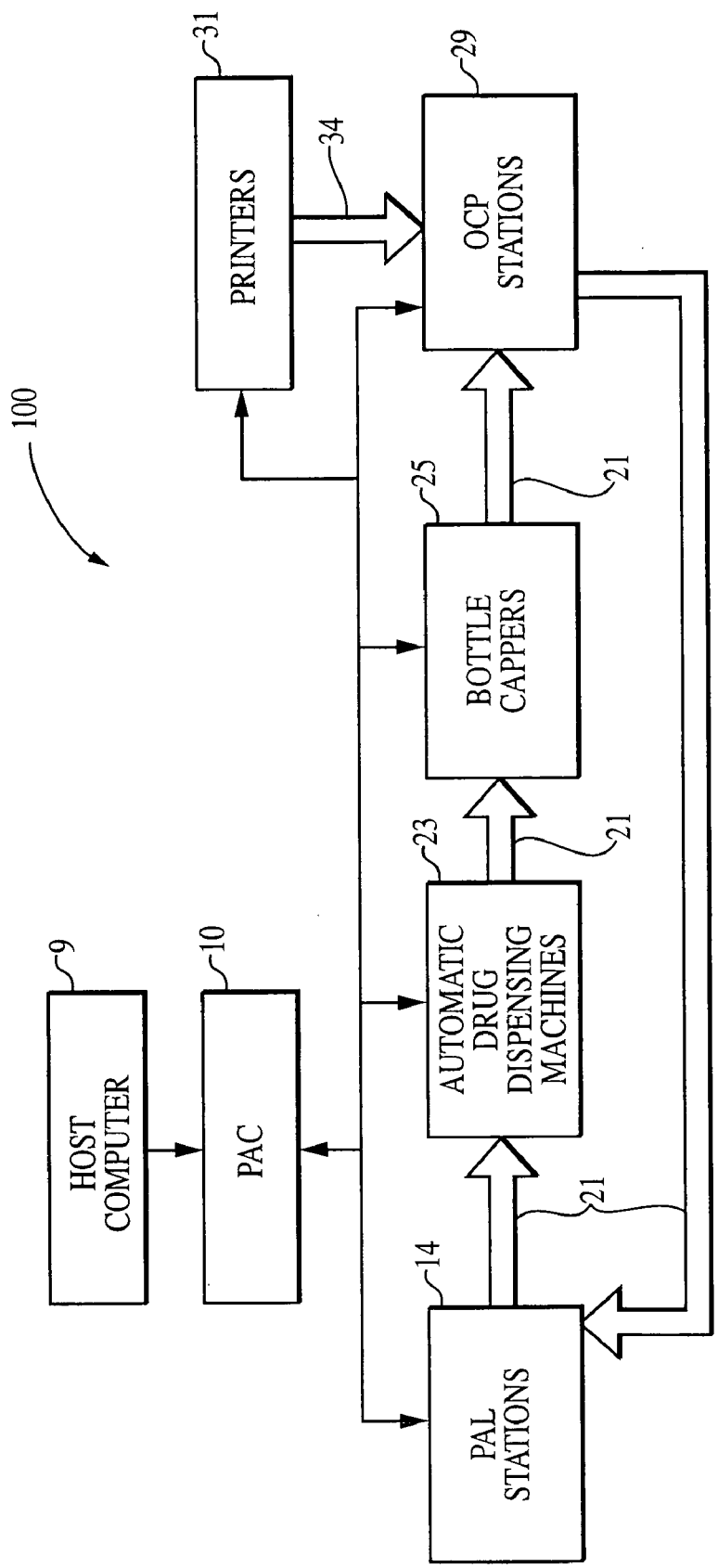
FIGS. 1A, 1B and 1C are exemplary diagrams illustrating a conventional automated pill dispenser that can utilize the bagger system disclosed herein.
Figure 1B:
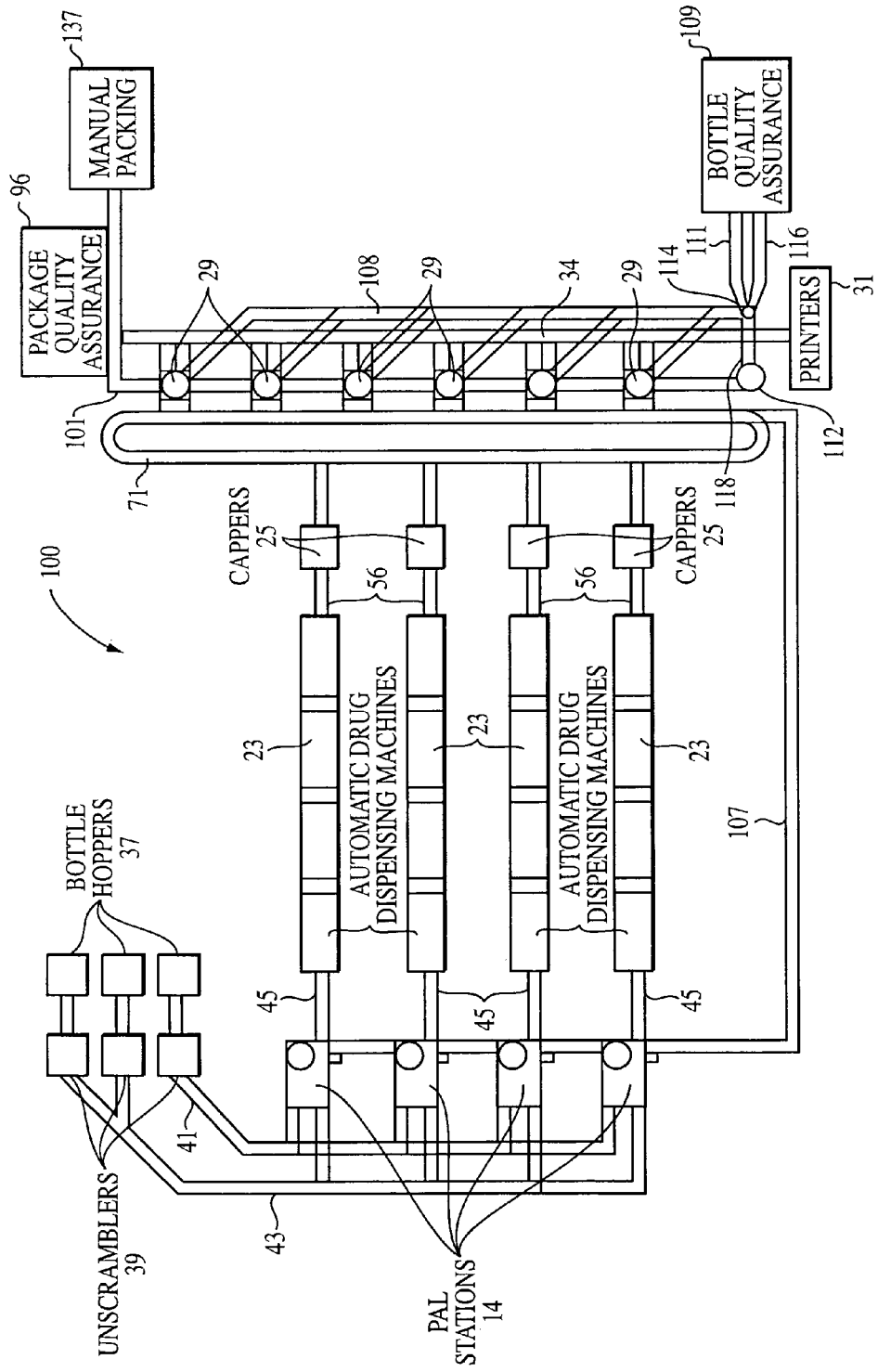

Patient prescription bottles that are to be automatically filled with the prescription drugs can be introduced to the automated system by hoppers (not shown, but the same as or similar to hoppers 37 shown in FIG. 1B) which receive the bottles in bulk form and automatically feed the bottles to unscramblers 39. For example, one hopper 37 and one of the unscramblers (not shown, but the same as or similar to an unscrambler 39 shown in FIG. 1B) can be used for relatively large bottles (e.g. 160 cc), and the remaining hoppers and unscramblers can be used for small bottles (e.g., 110 cc). Small bottles preferably can be used for a majority of the prescriptions. Any prescription orders that cannot be filled by using a large bottle can be filled by using multiple large and/or small bottles. In the unscramblers, the bottles are singulated and oriented so that the bottle opening first faces downward. The bottles are then, for example, righted and directed to PAL stations 14 on bottle conveyers (not shown, but the same as or similar to conveyors 41, 43 shown in FIG. 1B), one for large bottles and one for small bottles.

Conveyers 45, under control by PAC 10, carry the bottle carriers from the four PAL stations 14 to carrier buffers at the entrances of the four automatic drug dispensing machines 23 in which the tablets or capsules of the prescriptions are automatically dispensed into the prescription bottles under the control of PAC 10. Because of the organization provided by the carriers, the bottles are arranged into four columns approaching each automatic dispensing machine 23. Since there are, for example, four automatic dispensing machines 23, 16 parallel prescription bottle columns can approach the dispensing machines. In this embodiment, the four automatic drug dispensing machines each have 384 drug dispensers arranged four columns wide and 96 rows deep to provide a total of 1,536 pill dispensers. The automatic drug dispensing machines are similar to those described in the U.S. Pat. No. 5,660,305, which is hereby incorporated by reference. Each dispensing lane is divided into 32 buffer assemblies, each containing twelve drug dispensers oriented six on each side of a conveyer within the dispensing machine. Other standard pill dispensers may optionally be used.

The carrier will be released by PAL station 14 onto a conveyer 45 which carries the carrier loaded with the labeled empty prescription bottles to an automatic dispensing machine 23, of which there are, for example, four, one for each PAL station 14. When a carrier moves out of the last row position in a dispensing machine, all of the prescription bottles in that bottle carrier should be filled and a conveyer 56 transports the prescription bottles now filled with the prescriptions to a bottle capper 25.

Bottle quality assurance area 109 has several stations at which, for example, pharmacists can scan the bar code on the bottles and visually inspect the contents of the bottles. The scan of the bottle bar code will bring up a display on the pharmacist's terminal which preferably includes all the information regarding the particular prescription and order. Such information can include, for example, the drug name, and instructions which identify the reason for the verification. All of the bottles that pass this inspection can be inserted by the pharmacist on a bottle stream conveyer 111 to send the inspected bottles to the BSP station 112. Conveyer 108 leads to a star wheel diverter mechanism 114 which, optionally under the control of a controller for BSP station 112, deposits the bottle in a bottle stream conveyer 116 leading to the bottle quality assurance area 109 or into a bottle stream conveyer 118 leading to BSP station 112.

If the literature pack is on conveyer 34, but because of failure of the bar code reader (not shown) or the literature sorting mechanism (not shown), does not get diverted to BSP station 112, conveyer 34 will carry the literature package to package quality assurance area 96 where it can be manually added to the package or alternatively re-inserted into the process for grouping with the appropriate order. If, because of a malfunction, a literature envelope is not deflected by a deflector 89 (FIG. 1C), because of, for example, an improper bar code on the envelope, the envelope will continue on conveyer 34 to the end of the conveyer and be dumped into a receptacle at the package quality assurance station 96. If the bag does not contain a literature pack, then the bag is diverted into a tote (not shown) which will then be transported by a conveyer 34 to the package quality assurance station 96, where the shipping container will be assembled with the literature pack manually 137. Alternatively, the entire order may be aborted and attempted again as described above.

Figure 1C:
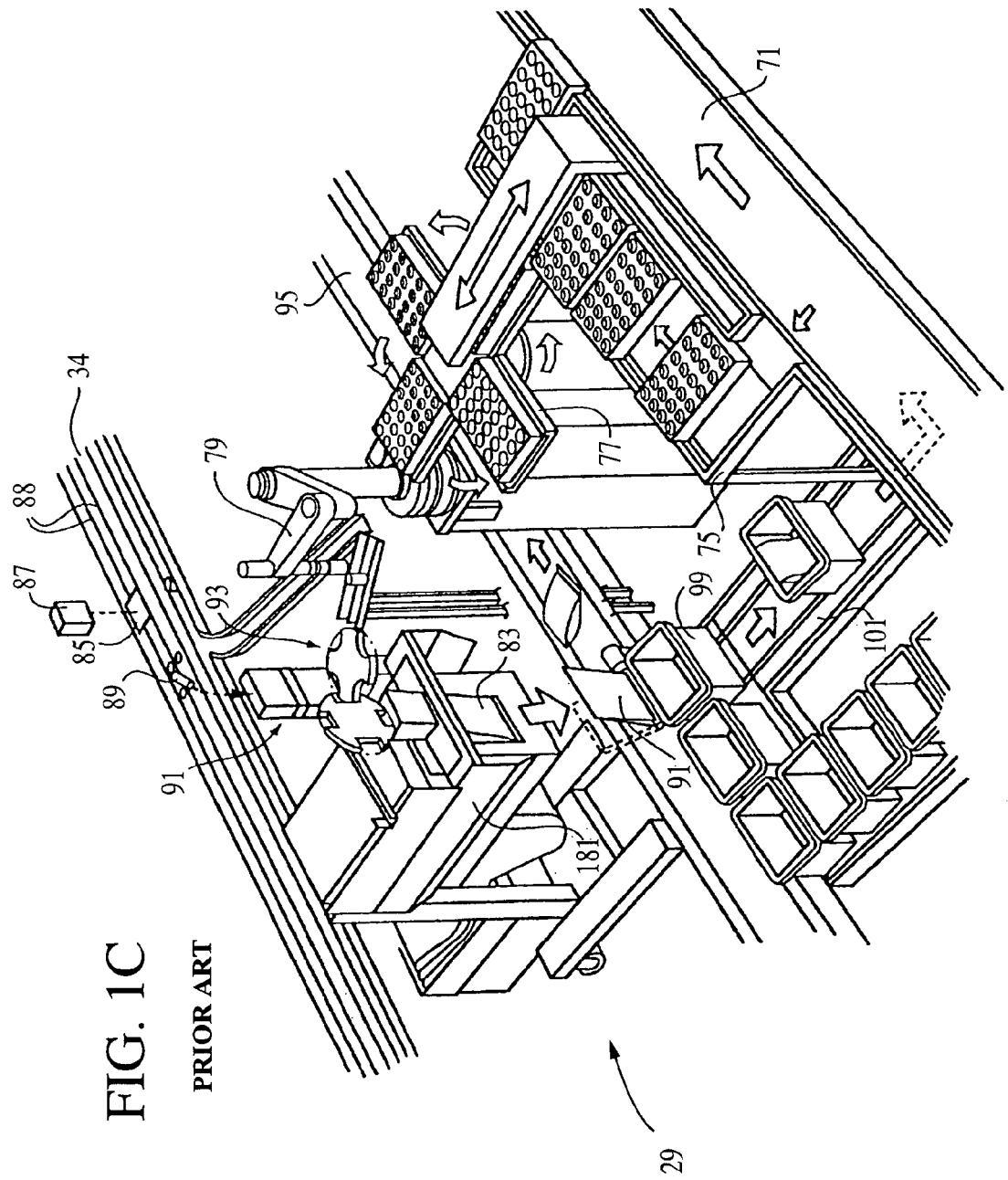

As shown in the OCP station 29 of FIG. 1C, the four carriers of a rank are first received in a carrier buffer 75 from which they are loaded onto a turntable 77. An RFID tag reader (not shown) verifies that the correct carriers are in place on turntable 77, which selectively rotates the carriers into a position to have the bottles removed by robotic arm 79 or other standard mechanism. OCP station 29 also contains equipment 91 for packing literature into shipping containers, which take the form of bags 83, along with the prescription bottles of a given order. OCP station 29 also includes a bagging machine 181 which presents the bags for successive orders to be loaded in sequence at a loading position. Bagging machine 181 can print a bar code identifying the order directly on each bag 83. The printed data may include the mailing address to which the shipping container is to be sent.

Bag 83 is shown at the loading position with its mouth open. The opening of the mouth of bag 83 can be accomplished by a standard blower (not shown) provided as part of bagging machine 181 or other standard mechanisms. Conveyer 34 brings envelopes 85 containing literature to be packed in shipping containers to OCP station 29 in the reverse sequence that the patient orders are to be packed at that OCP station 29 for a given rank of carriers. At OCP station 29, literature conveyor 34 can be in the form of a standard literature sortation system of the type used in mail sortation by the U.S. Post Office. The literature sortation system can include a pair of belts 88 that pass the envelopes along from station to station. Deflector 89 can optionally be located between each pair of belts 88, and be controlled by the OCP station controller to deflect selected literature envelopes into a literature dispensing mechanism 91.

When a rank of carriers is directed to a given OCP station 29 by PAC 10 from bottle cappers 25, PAC 10 can send an unload message to the controller for the OCP station 29. The unload message can contain an indication of the sequence that the orders are to be unloaded from the rank of carriers at the station, as well as containing the information as to the scheduled position of the bottles of each order in the four carriers of the rank of carriers to be unloaded. At the same time that PAC 10 sends an unload message to the controller of the OCP station 29, it can send a corresponding autopublish message to printers 31. The message can contain the information to be printed for the complete orders contained in the rank of carriers being sent to an OCP station 29. The autopublish message will also contain the sequence in which the corresponding orders are to be unloaded at the OCP station 29. In response to the autopublish message, one of the printers 31 will print literature for the orders and deposit the literature packs for the orders on literature conveyer 34 in reverse order from that in which the orders are to be unloaded at the OCP station 29. Other sequences and/or orders of the steps described above may optionally be used.

Each literature pack is preferably enclosed in an envelope having a die cut window through which a bar code is readable by a bar code reader 87. The bar code can be printed by an appropriate printer 31 to identify the order for which the literature pack is printed. As the envelopes containing literature packs are carried past the OCP station 29 in the literature sortation system, the bar code readable through the window in each envelope will be read by a bar code reader 87, that can verify that the bar code coincides with an order in the unload message received by the controller for OCP station 2. The controller for OCP station 29 will then cause deflector 89 to deflect the envelope into literature dispensing mechanism 91. Since the conveyor brings the literature envelopes to an OCP station 29 in, for example, the reverse sequence that the corresponding patient order is to be packed at the packing station, the envelopes will be packed into the dispensing mechanism in that sequence. When bag 83 is ready to be packed at OCP station 29, literature dispensing mechanism 91 first inserts a literature envelope into the bag 83 where it will be positioned at one side of the bag (by, e.g., gravity). This effect is achieved by orienting the bag 83 at a slight tilted position at bagging machine 181. After the literature has been inserted, robotic arm 79 or other mechanism unloads the bottles of the order from the scheduled positions in the four carriers on the turntable in accordance with the unload message. Robotic arm 79 preferably includes a bar code reader so that each time a bottle is lifted out of a carrier by robotic arm 79, the label on the bottle is read and verified.

The prescription bottles are then loaded into the bag 83 by a standard bottle loading mechanism 93. When the shipping containers 83 have been verified and filled with a literature pack and with a patient's order, the bag is sealed and dropped onto a conveyer 95 which carries the sealed shipping container to a mailing area where the bag is read and logged and then mailed to the customer. If the bag 83 does not contain a literature pack, then the bag is diverted into a tote 99 which will then be transported by a conveyer 101 to the package quality assurance station 96 where the shipping container will be assembled with the literature pack, for example, manually. Alternatively, the order can be aborted, and attempted again through the automated process described herein. As shown in FIG. 3A, bagger 181 can be used with either or both of system 100 and ALPS system 250.

Figure 3B:
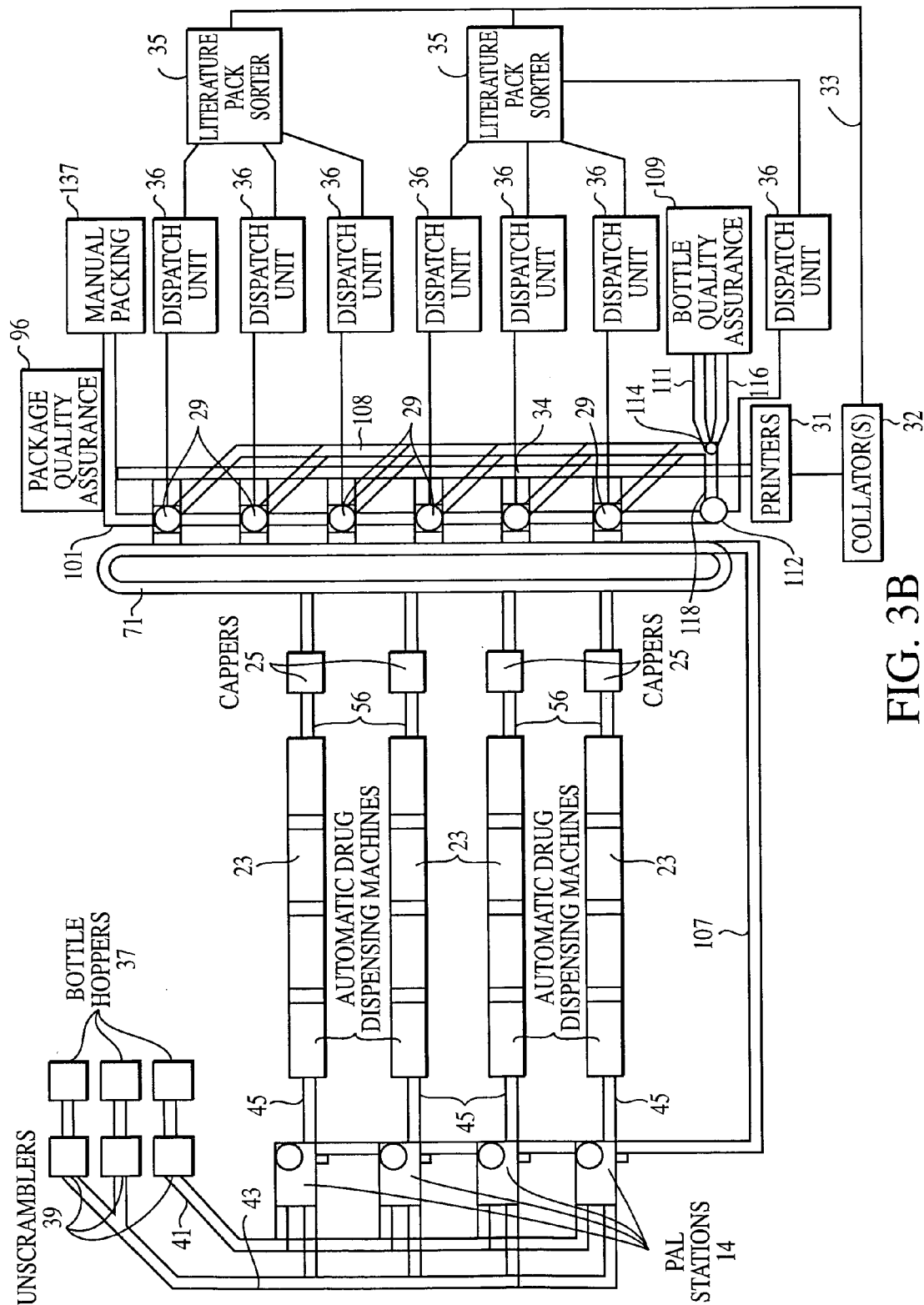
FIG. 3B is an exemplary diagram illustrating an aspect of an automated pill dispenser that can be used with the present invention.

FIG. 3B is similar to FIG. 1B, and shows exemplary aspects of the automated pill dispensing system 310 shown in FIG. 3A. In operation, one or more literature packs can be printed on a printer 31, and sent to a collator 32 for collation into individual literature packs. More than one collator 32 can optionally be used. Once literature packs are collated, they can travel, for example, on a standard pinchbelt conveyor 33 to a literature pack sorter 35, where they are sorted into literature pack batches. Although two literature pack sorters 35 are shown, any number of literature pack sorters can be utilized to suit, for example, cost and/or volume considerations.

On command from, for example, an OCP station 29, the literature pack batches can optionally be manually transferred from the one or more sorters 35 to a dispatch unit 36. Again, any number of dispatch units can be utilized to accommodate, for example, manufacturing, facility size and/or cost requirements or constraints. Dispatch units 36 can feed the literature packs to an OCP station 29.

Figure 4A:
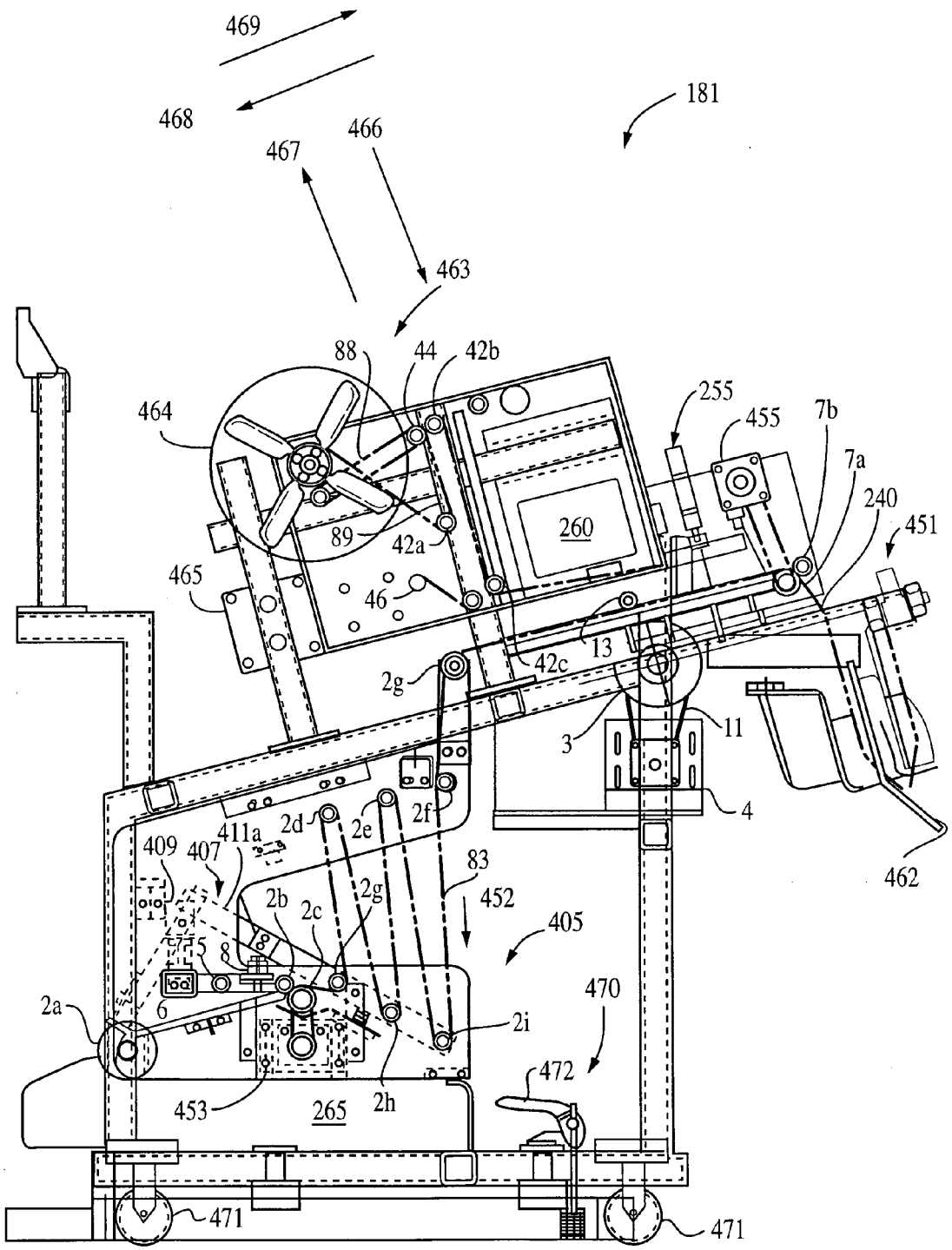
FIG. 4A is an elevation view of an exemplary bagger.

When system 310 detects (and/or suspects) a problem with an order (e.g., a wrong shipping address, incorrect prescription drug(s), and/or incorrect prescription quantity), an OCP station 29 can place the order in a bag, and divert the bag into, for example, a standard tote (not shown). The tote can be transported by, for example, conveyer 101 to package quality assurance station 96, where a quality assurance person can inspect the order and correct anything that might be wrong (as discussed above) with the order. After inspection and corrective action, the quality assurance person at station 96 can take additional action(s) to ensure that the properly filled order is shipped to the patient/client. An embodiment of the bagger 181 in accordance with the present invention (as will be discussed herein), can interface with, for example, a dispensing unit 36 and an OCP station 29, to perform the bagging operations described herein. A bagger 181 (FIG. 4A) can optionally interface with, for example, each OCP 29—dispatch unit 36 combination. Turning now to FIG. 4A, an exemplary side view of bagger 181 is shown. Bagger 181 is a separate unit that, in an embodiment, is detachable and/or interchangeable with, for example, an OCP station 29 (of FIGS. 1A–1C) and/or ALPS 250 (of FIGS. 2A–2E). Bagger 181 feeds incoming bags 83, preferably but optionally from a preloaded fan-folded blank bag stock (not shown) that can be stored in bag supply 265.

Figure 4B:
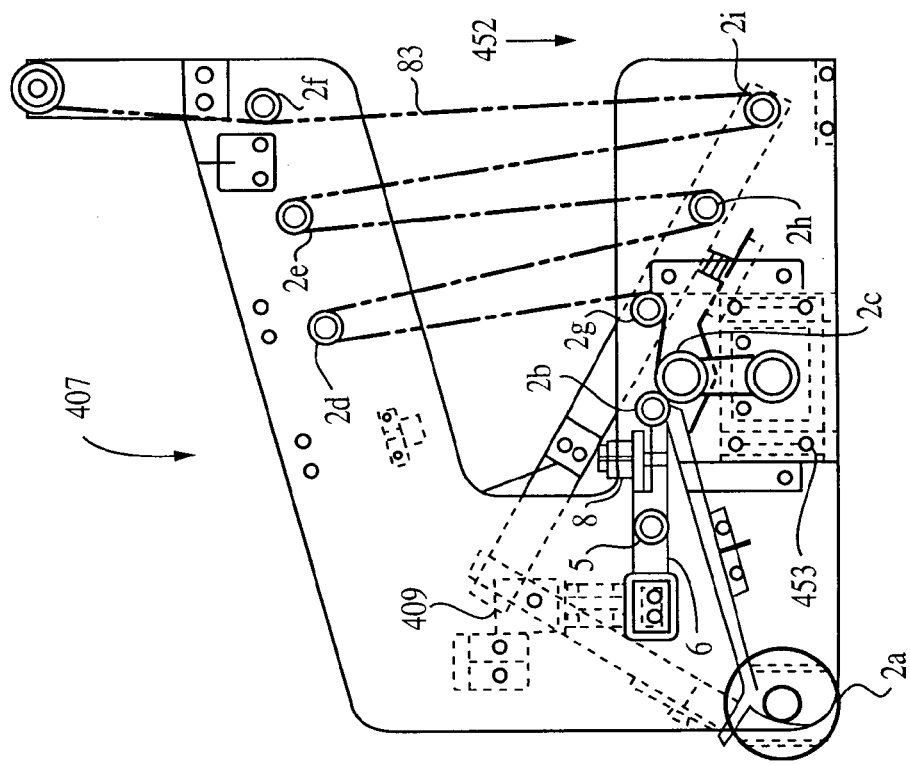
FIG. 4B is an exemplary bag feed dancer assembly of the bagger.
Figure 4C:
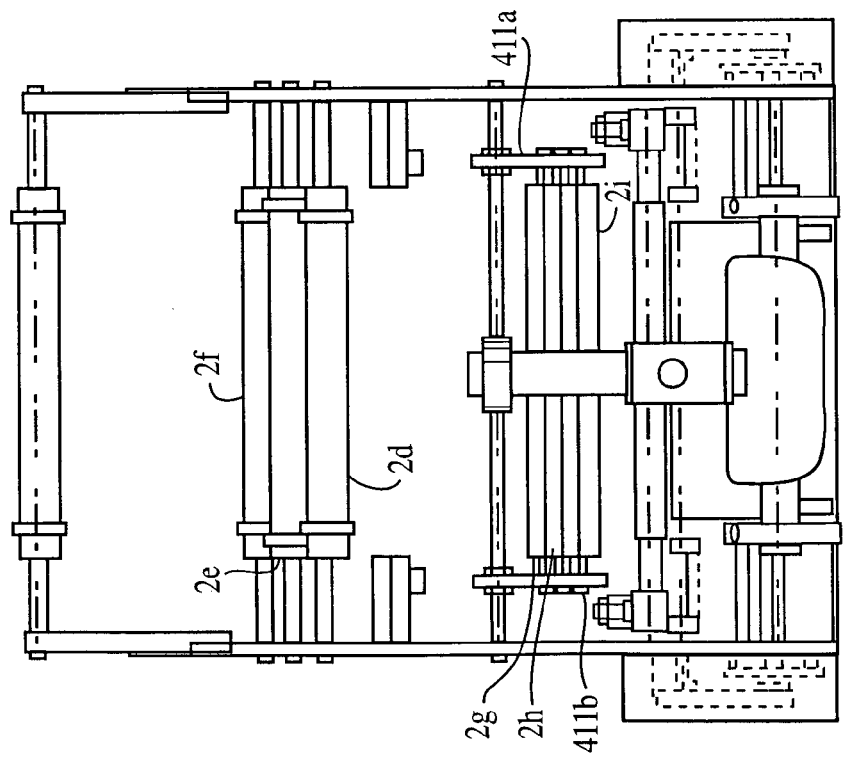
FIG. 4C is a cross section view of an exemplary bagger.

Bags 83 are advanced by motor 453 through a series of rollers 2a, 2b, 2c, to bag feed dancer 407 and associated rollers 2d–2i. Motor 453 can optionally be a variable speed motor. FIG. 4B shows a larger view of the bag feed dancer 407 shown in FIG. 4A. FIG. 4C shows a view of bagger 181, showing rollers 2d–2i. In FIG. 4A, arm 411a is shown on a first side of rollers 2g, 2h, 2i. In FIG. 4C, arm 411b is shown on an opposing side of rollers 2g, 2h, 2i.

Bag feed dancer 407 accumulates bag 83 film and provides tension so that the perforation that separates the two bags 83 will not be torn during bag indexing (as will be described herein). Motor 453 can be used to lock, as well as drive, roller 2c. When roller 2c is locked, motor 455 can be used to activate index roller 7a which, in combination with roller 7b, transports the bag 83 film. Because rollers 2b and 2c are locked, dancer 407 is raised when index roller 7a is activated. When dancer 407 is raised a predetermined amount (to, e.g., account for the length of the bags 83), a sensor 8 (e.g., a limit switch) located above shaft 6 can be used to activate motor 453. Then, motor 453 is activated so rollers 2b, 2c feed bag 83 film into dancer rollers 2d–2i until dancer 407 drops a sufficient amount for sensor 8 to stop motor 453. Rollers 2b, 2c, can optionally be separated each cycle by pneumatic cylinder 409, to allow bag 83 film to realign between rollers 2b, 2c.

As bags 83 are being transported toward printer 260, label dancer assembly 463 controls label tension into printer 260. An embodiment of label dancer assembly 463 includes roller 42a, dancer 42b, and roller 42c, which can be used to accumulate labels between label roll 464 and printer 260. A control computer (not shown) can supply data in a conventional manner to printer 260. In an embodiment, printer 260 can be a SATO label printer (SATO America, Inc., Charlotte, N.C.).

Printer 260 prints the correct label for bag 83 corresponding to a prescription order. Printer 260 can receive data from, for example, computer 9 (FIG. 3A) and/or computer 201 (FIGS. 2A, 3). At the start of a print cycle, a drive (not shown) of printer 260 rolls a label back (in the direction of arrow 468) approximately 0.25 inch to optionally allow printing of the leading edge of the label. Printer 260 then pulls the label forward (in the direction of arrow 469) from the label dancer assembly 463 and across the print head, optionally at a rate of, for example, 6 inches per second. While the label moves forward, motor 465 locks label roll 464, which causes dancer 42b and cam 44, each mounted on shaft 88, to drop in the direction of arrow 466. Dancer 42b is preferably under spring tension, biasing dancer 42b in the direction of arrow 467. Motor 465 can optionally be connected to label roll 464 by, for example, a belt (not shown).

As cam 44 moves in the direction of arrow 466, it comes into contact with, for example a switch (not shown), optionally mounted on surface 89. When cam 44 contacts the switch, motor 465 is activated to turn label roll 464 to dispense another bag 88, which causes dancer 42b to rise in the direction of arrow 467. The printed label can exit printer 260, and optionally rotate about, for example, a standard scraper bar (not shown), where the label backing material is stripped and accumulated on label take-up roller 46.

After printing, a barcode scanner (not shown) can optionally be utilized and be positioned downstream of printer 260 to read the barcode on the printed label to verify that the label was printed correctly before the label is delivered to tamp 255. If the label did not print correctly, bag 81 and the label can be rejected, and a new label can be printed and placed on the next bag 81. After the label is printed and optionally verified, the label proceeds to tamp 255, which stages the printed label and applies the label to bag 83.

Figure 5:
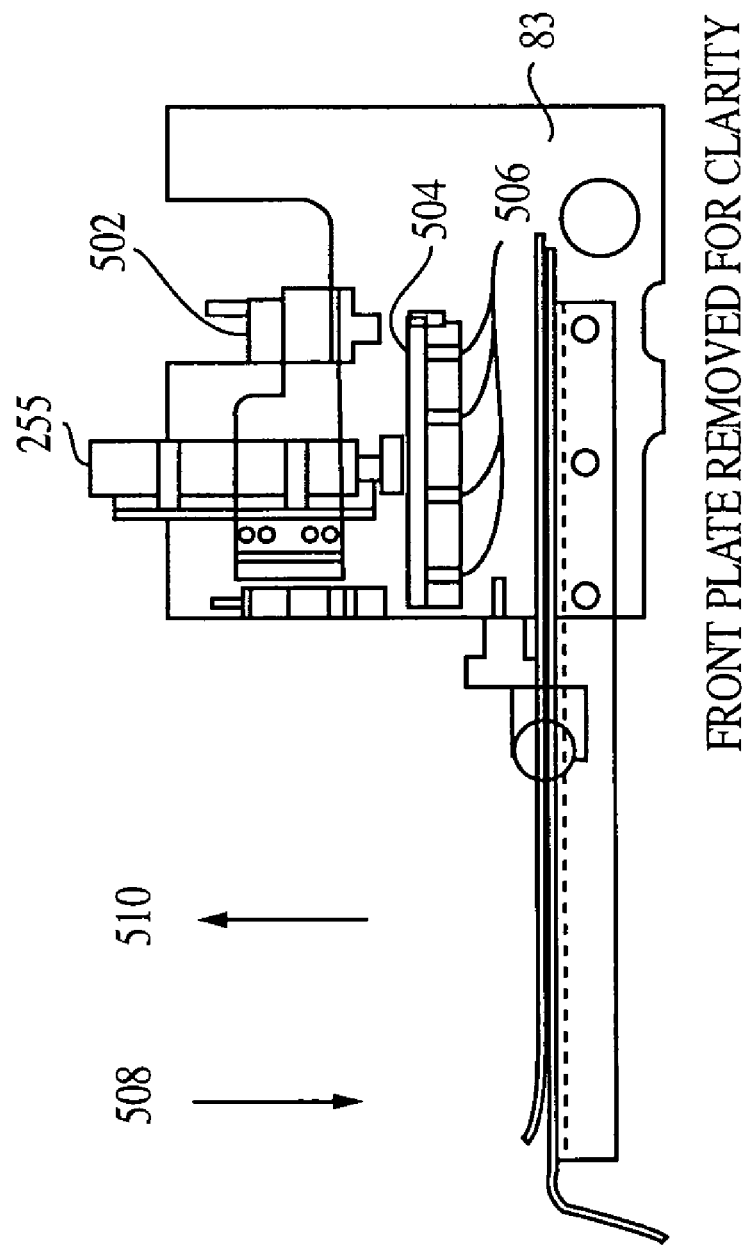
FIG. 5 is an exemplary embodiment of a tamp pad assembly of the bagger.

Referring now to tamp 255 shown in FIG. 5, a grid arrangement of holes 506, optionally supplied with vacuum in the direction of arrow 510, can be used to hold the label on tamp pad 504 until bag 83 is in position. Following an index servo move (explained herein) that places bag 83 into a position for label application, tamp pad 504 moves in the direction of arrow 508 to place the label on bag 83 positioned therebeneath. The vacuum air can be turned off (or reduced) when tamp pad 504 reaches bag 83. Proximity sensors (not shown) can optionally be used to sense tamp pad 504 movement. For example, a reflector (not shown) can be placed at or near an edge of tamp pad 504, and an emitter/receiver (not shown) can be placed to operate in conjunction with the reflector.

In one embodiment, when the label is in proper position on tamp pad 504, the emitter/receiver will not detect a return signal from the reflector, thereby indicating that the label is in a proper position. If the reflector and emitter/receiver detect that label is not correctly positioned on tamp pad 504, bagger 181 can fault. After an operator acknowledges the label position fault, the fault will clear and bagger 181 can then perform the tamping. A valve, optionally connecting with pneumatic cylinder 502, can be used to cycle tamp pad 805 up and down.

After labeling, and referring back to FIG. 4A, index rolls 7a, 7b pull bag 83 film (in the direction or arrow 469) from infeed dancer 407 to index a bag 83 prior to opening. Index rolls 7a, 7b can also retract bag 83 (in the direction of arrow 468) to break the bag 83 along a perforation. Index rolls 7a, 7b can be driven by, for example, a standard Yaskawa servo motor 455 (Yaskawa Electric America, Inc., Waukegan, Ill.) and associated control system (not shown).

To perform an index, a perforation between bags 83 is detected by, for example, a standard optical scanner 13. In an embodiment, a Keyence FS-V1 fiber optic sensor (Keyence Corporation, Osaka, Japan) can be used as the optical scanner 13. The bagger control system (not shown) can activate motor 455 so that index rolls 7a, 7b move bag 83 until a perforation is detected by scanner 13. The perforation detected will preferably be on a trailing end of bag 83. When a bag 83 perforation is detected, the position of the perforation is also known by the bagger control system. Since the length of the bag 83, bag 83 position, and the position of, for example, seal bar assembly 240 are known, the bagger control system can activate motor 455 to forward the bag 83 perforation a predetermined amount (e.g., an absolute move) such that the perforation is positioned so that fingers 608a, 608b (FIG. 6) can grasp the bag 83 perforation and open the bag 83. In an embodiment, computer 9 and/or computer 201 can also be used to control index operations.

Figure 6:
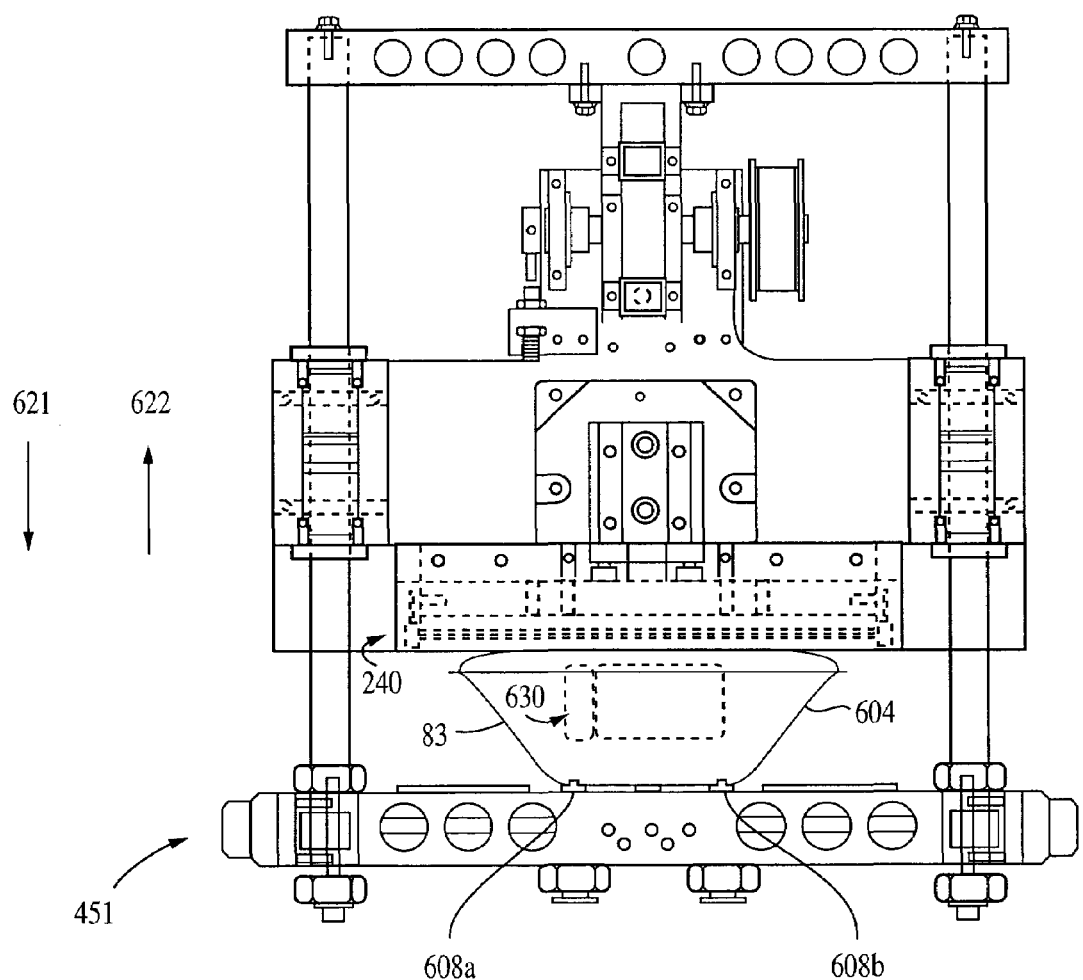
FIG. 6 is an exemplary embodiment of a seal bar assembly of the bagger.

In particular, and referring now to FIG. 6, when a bag 83 is fed to load position 604, fingers 608a, 608b, in conjunction with jaw assembly 451, move in the direction of arrow 622. Upon grasping a portion of bag 83 at or near, for example, a perforation of bag 83, fingers 608a, 608b move in the direction of arrow 621 to open bag 83. In an embodiment, while one bag 83 is being tamped to have a label placed thereon, another bag, already having been tamped, is in load position 604.

In an embodiment, jaw 451 can be controlled by a controller (not shown), optionally configured to cut power to jaw 451 when, for example, an emergency stop button (not shown) is activated and/or a guard door (not shown) is opened. The controller is also preferably configured so that, if stopped, jaw 451 position is held, and bagger 181 can resume its previous cycle upon restarting. For example, when power to jaw 451 is restored (e.g., after an emergency stop), jaw 451 can be sent to a "home" position. If action was taken to stop the cycle (e.g., a "Cycle Stop" button is pressed), jaw 451 can return to its last position, and the bagger cycle can resume when action is taken to start the cycle (e.g., a "Cycle Start" button is pressed).

Fingers 608a, 608b can be controlled by pressure regulated pneumatic valves (not shown) to pull bag 83 open (in direction of arrow 621) for filling. Fingers 608a, 608b can, for example, optionally rotate about an axis (not shown) of jaw 451. As jaw 451 moves in the direction of arrow 621 to open a bag 83, fingers 608a, 608b can be timed to contact a perforation of bag 83. As shown in FIG. 4A, jaw 451 is optionally cam 3 driven by, for example, motor 4, and belt 11. Motor 4 can optionally be a standard Yaskawa servo motor.

A vacuum assist suction cup (not shown) can optionally be provided, for example, at or near the center of jaw 451 to facilitate opening bag 83. The vacuum can be used to pull bag 83 perforation open (in the direction of arrow 621) in cooperation with fingers 608a, 608b. As the vacuum and/or jaw 451 move to open bag 83, fingers 608a, 608b can, for example, rotate about an axis to contact bag 83 perforation, and open bag 83.

Figure 7:
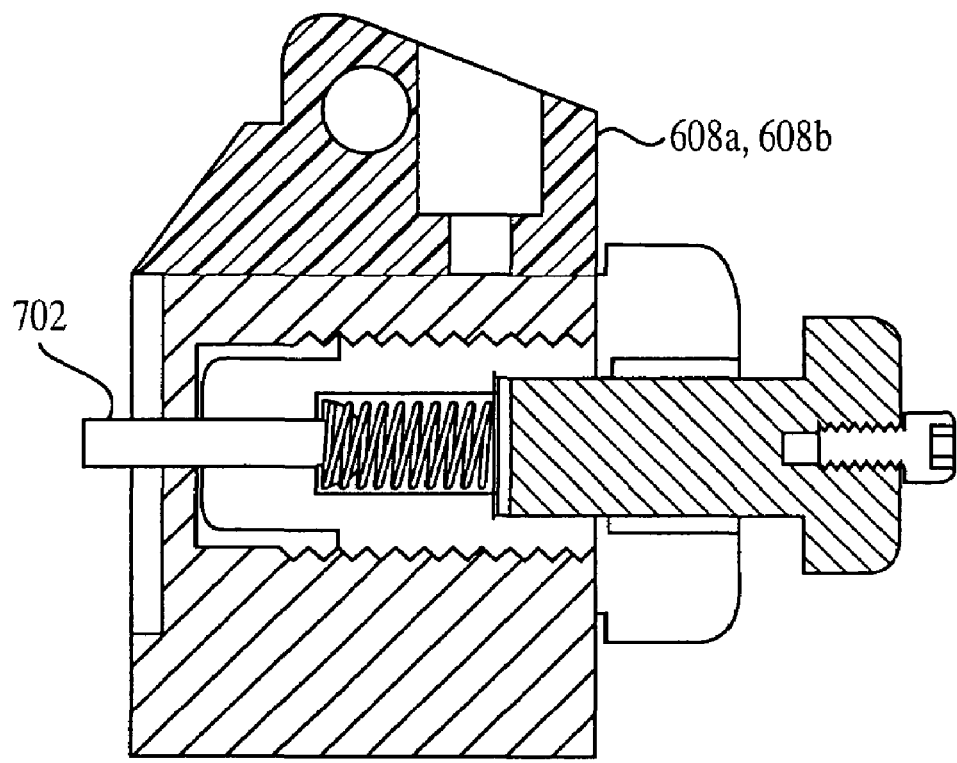
FIG. 7 is an exemplary embodiment of a bag open finger.

In an embodiment, fingers 608a, 608b and axle can be charged (e.g., with 24 VDC) and electrically isolated from ground by a rubber coupling (from e.g., Lovejoy Corporation, Downers Grove, Ill.). As shown in FIG. 7, a spring loaded pin 702 can be provided under fingers 608a, 608b to provide a path to ground for the signal, indicating that bag 83 is not present under fingers 608a, 608b and that bag 83 is not properly opened.

During the bag 83 open cycle, bagger 181 can try, for example, up to three times (or any other number of predetermined times) to properly open bag 83. If bag 83 cannot be opened, bag 83 can be ejected, and a new bag 83 can be indexed to begin the cycle again. If bag 83 slips out or is otherwise removed from under finger 608a, 608b during the filling cycle, allowing a path to ground for the signal (e.g., 24 VDC), a "Loss of Grip" alarm can optionally be generated.

Referring back to FIG. 6, as fingers 608a, 608b are opening bag 83, fingers 608a, 608b can optionally be positioned to keep the outside edge of bag 83 contacting jaw 451 open to maximize the opening available for dispensing product(s) 630 into bag 83. Fingers 608a, 608b can close (return to center "home" position) as jaw 451 begins to move in the direction of arrow 622 to complete bag 83 sealing. Motor 4 and cam 3 can then be used to move jaw 451 toward seal bar assembly 240.

Once bag 83 has been filled with one or more literature packs and/or one or more pharmaceutical containers, index rolls 7a, 7b shown in FIG. 4a rotate in the direction of arrow 468 to break the bag 83 perforation.

Figure 8A:
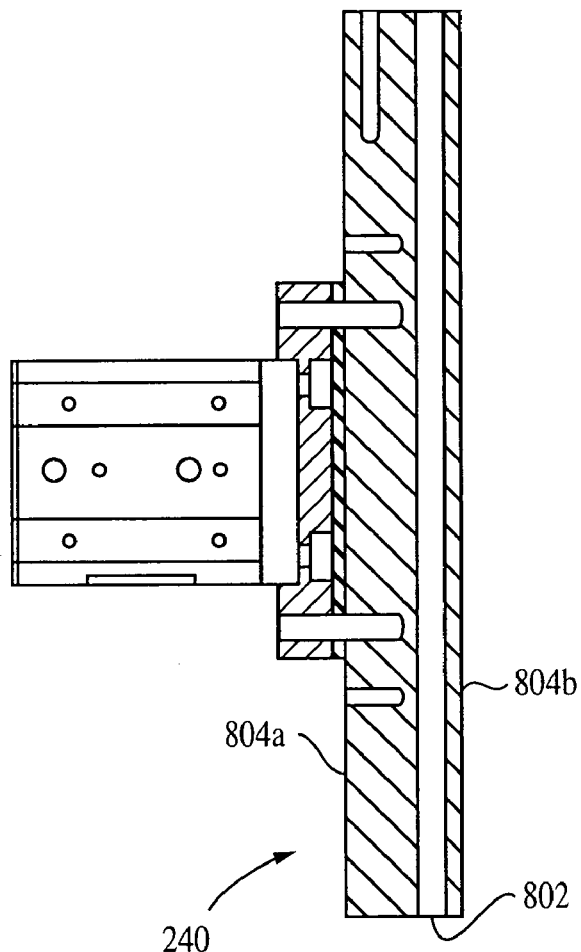
FIG. 8A is a top view of an exemplary aspect of the seal bar assembly.
Figure 8B:
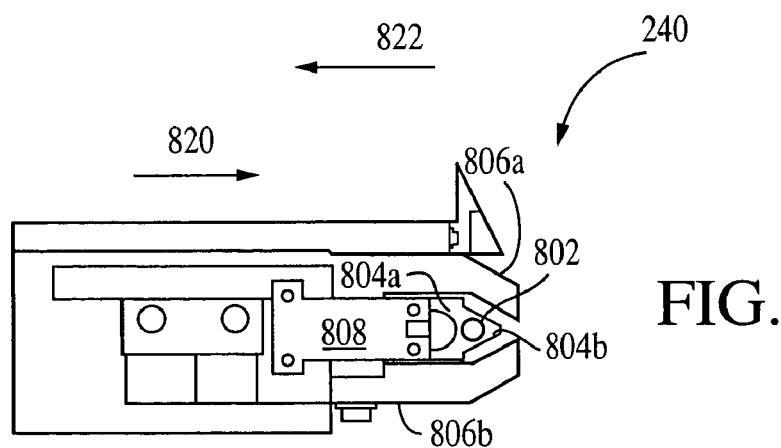
FIG. 8B is an elevation view of an exemplary aspect of the seal bar assembly.

Seal bar assembly 240, shown in FIGS. 6, 8A and 8B, seals bag 83 after filling. FIGS. 8A and 8B show a top view and elevation view, respectively, of seal bar assembly 240. A temperature controller (not shown) can be used to heat and control heater element 804a, 804b shown in FIGS. 8A and 8B to maintain seal bar 802 at a specific set point temperature (e.g., approximately 350–420 deg. F) to melt or fuse bag 83 film. The set point temperature can optionally be manually entered into the temperature controller, which cycles power on/off through an output contact in the controller, to heat the heater element 804a, 804b as required to maintain the seal bar 802 temperature at or near the set point. In an embodiment, a "Seal Bar Temp. Out of Range" alarm can sound when, for example, seal bar 802 temperature deviates more than a predetermined amount from the set point (e.g., more than +/−2 deg). Fingers 608a, 608b can also optionally serve to keep bag 82 spread during sealing to prevent wrinkles. Upper housing 806a and lower housing 806b partially surround heater element 804a, 804b and rod 802.

To seal bag 83, jaw 451, for example, moves in the direction of arrow 622 shown in FIG. 6, to close bag 83. When jaw 451 has moved a sufficient distance in the direction of arrow 622, a seal bar valve (not shown) can be used to power, for example, an air cylinder 808 to push rod 802, heater element 804a, 804b in the direction of arrow 820, preferably a predetermined distance (e.g., one half inch) and for a predetermined time (e.g., 0.25 seconds), thereby causing bag 83 to melt and/or fuse together. Other standard sealing processes may optionally be used.

Seal bar assembly 240 can then move in the direction of arrow 822 to return to its rest position. A proximity sensor can optionally be utilized to verify that seal bar assembly 240 has moved properly during the cycle. Once bag 83 is sealed, it can be placed onto, for example, a discharge conveyor (e.g., conveyor 108 shown in FIG. 1B and/or conveyor 1519 shown in FIG. 2B) for transfer to, for example, the mail conveyor or placement into a tote, as appropriate.

Tension is maintained when bags 83 are in contact with infeed dancers 2d–2i. Tension can cause bag 83, for example, to be pulled backward (in the direction of arrow 452) after bag 83 has been dropped from seal bar assembly 240 so that the next bag label can be indexed and tamped (as previously discussed) in the correct position on the next bag 83. Tension control screws (not shown) can optionally be provided on, for example, each side of upper roller 2b to keep bags 83 aligned into dancer 407.

As shown in FIG. 4A, a docking system 470 can be used to properly position and secure bagger 181 to an OCP station 29. The docking station 470 advantageously allows interchangeability of baggers 181 between various OCP stations 29.

In an embodiment, an OCP station 29 can have prepositioned floor track guides to direct the guide wheels 471 of bagger 181 into position. Once the bagger 181 is positioned in the track, it can be docked using, for example, hand crank 472. After docking, down clamps (not shown) can be used to hold bagger 181 to the track to, for example, minimize vibration. A limit switch (not shown) can optionally be used in conjunction with docking so that when bagger 181 is undocked, bagger 181 stops operation.

Figure 9A:
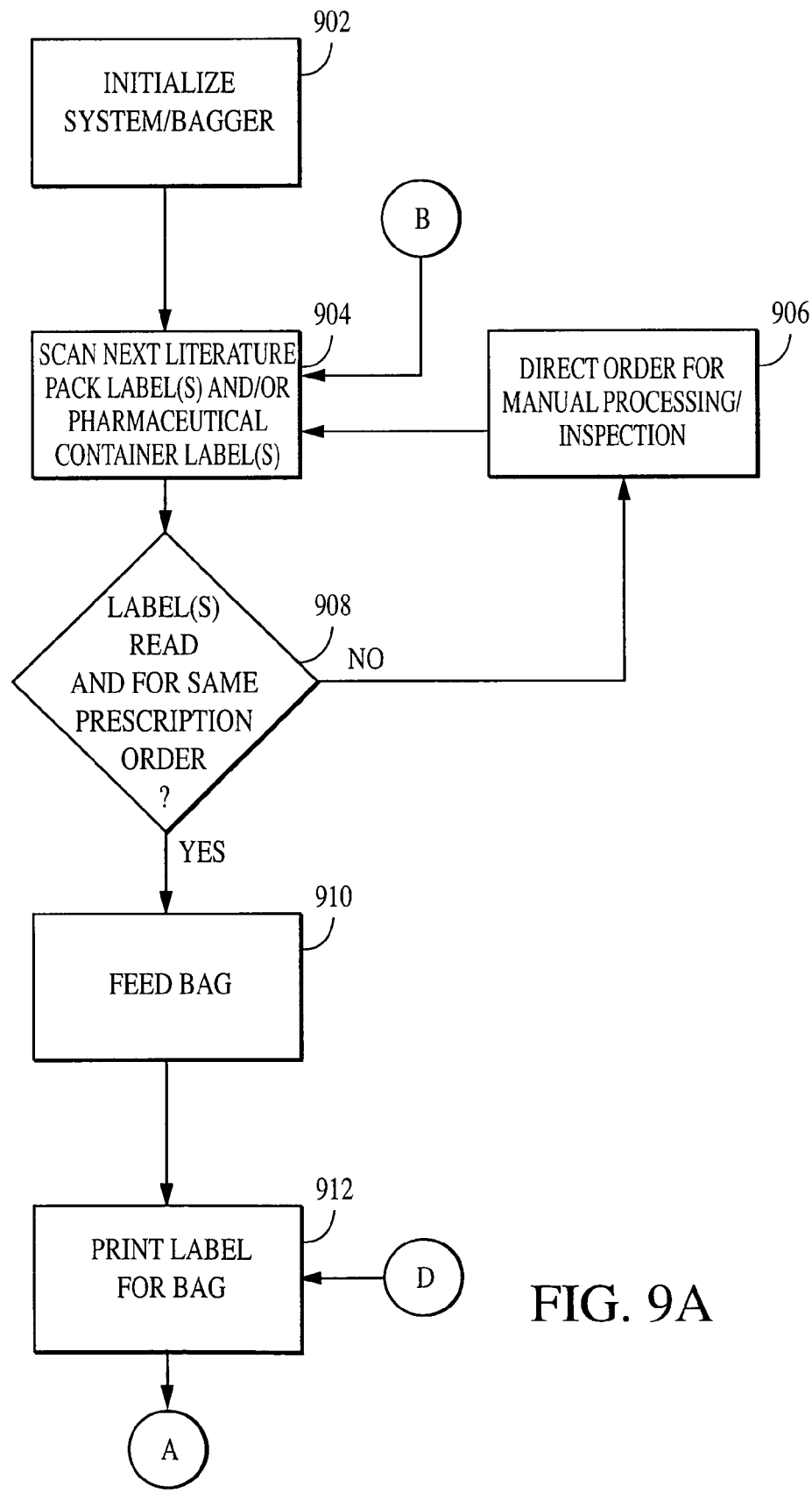
FIGS. 9A, 9B and 9C, taken together, is an exemplary embodiment of a flow chart of a method of operation of the bagger.
Figure 9B:
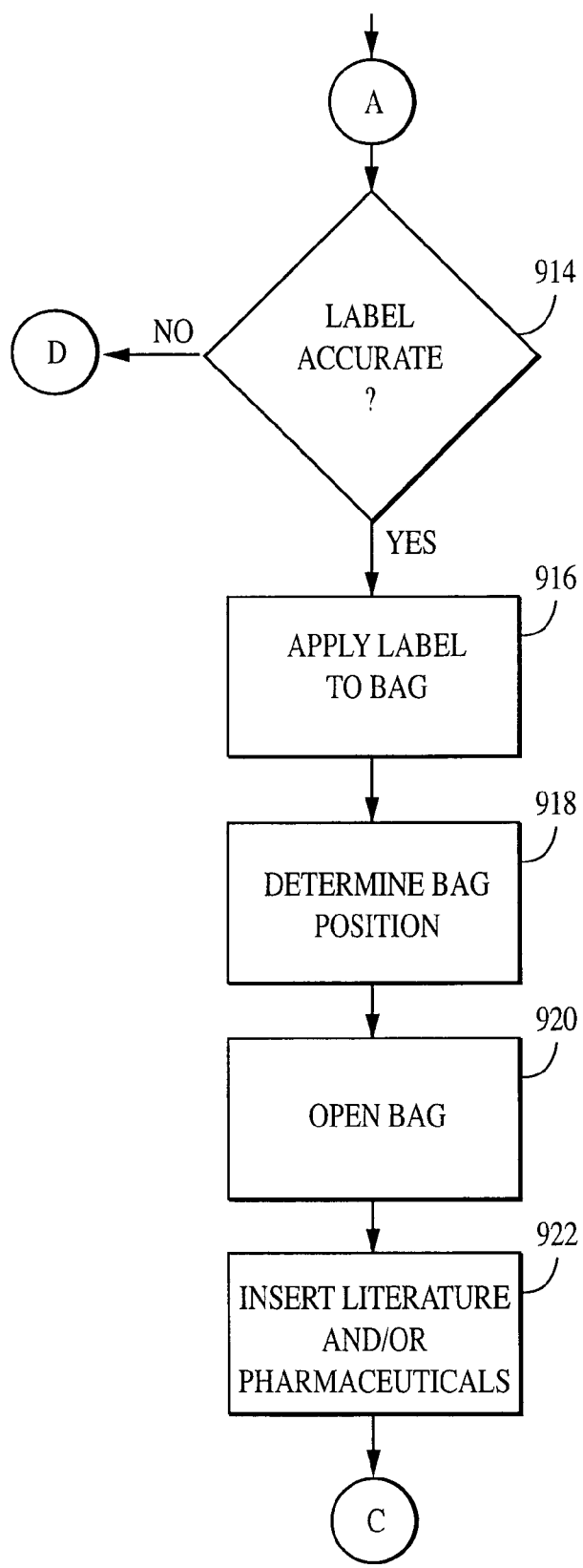
Figure 9C:
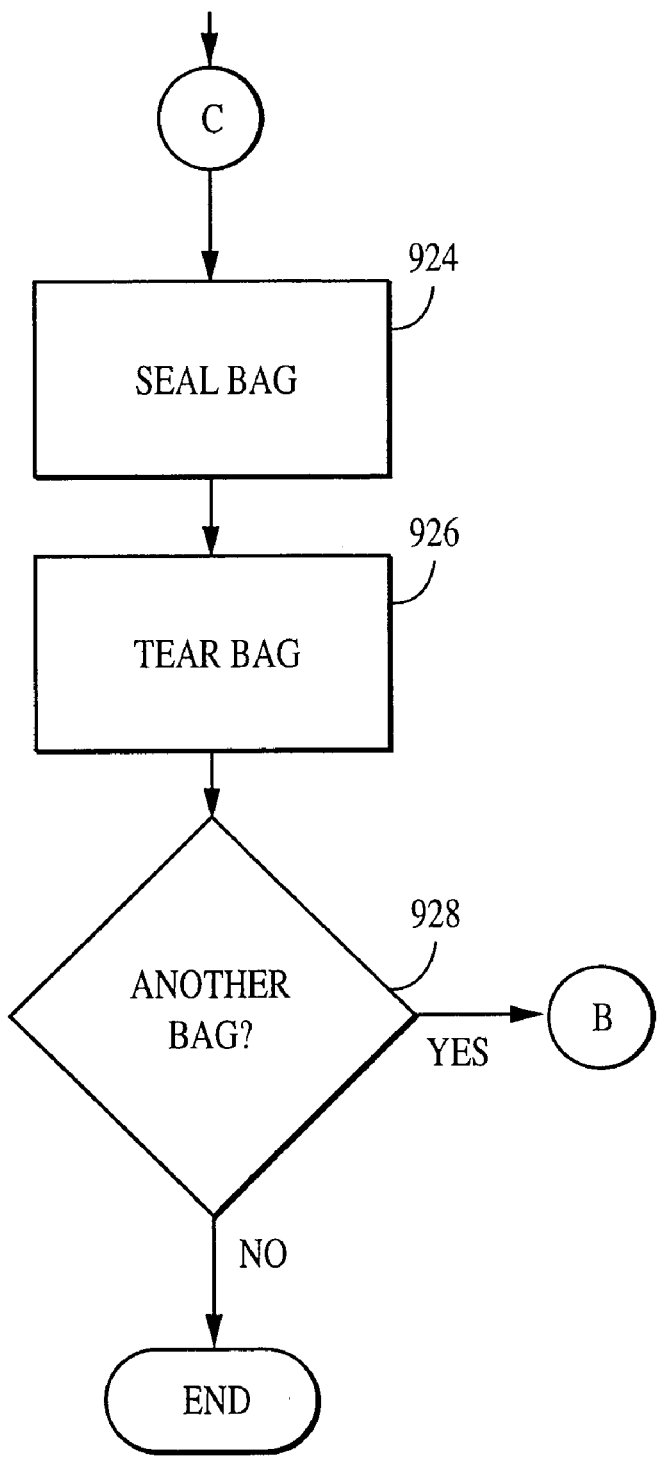

FIGS. 9A, 9B and 9C, taken together, is an exemplary embodiment of a flow chart of a method of operation of the bagger. At step 902, system 100, ALPS 250 and/or bagger 181 is initialized for operation. Initialization can include, for example, power up and diagnostic checks.

At step 904, the next literature pack label(s) and/or pharmaceutical container labels are scanned. If, at step 908, it is determined that there is a mismatch between, for example, a literature pack label and a pharmaceutical container label, then the order can be manually processed at manual packing station 137 and/or placed on tote conveyor 1521 (FIG. 2B), which can transfer any bottles to an operator who can manually fill the order. If at step 908 it is determined that matching literature pack and pharmaceutical container labels exist, then a bag 83 can be fed through bagger 181 at step 910. Printer 260 can print a bag 83 label corresponding to the prescription order.

The printed bag 83 label can be scanned by scanner (not shown) positioned downstream of printer 260 to determine of the label is accurate and corresponds to the prescription order. If the label is not accurate, another label can be printed at step 912. If the label is accurate, the label can be applied to bag 83 by tamp 255.

At step 918, the bag position can be determined by indexing. For example, a perforation between bags can be read by a scanner to determine the location of the bag. After indexing, the bag 83 is forwarded to an open position, where jaw 451 and fingers 608a, 608b can open the bag 83.

At step 922, any literature associated with the prescription order, and any pharmaceutical containers associated with the prescription order are inserted into bag 83. At step 924, seal bar assembly 240 can be used to seal the bag 83.

At step 926, index rolls 7a, 7b (FIG. 7A) can be used to retract bag 83 (in the direction of arrow 468, FIG. 4A) and/or to break the bag 83 along a perforation. The index rolls 7a, 7b can be driven by, for example, a servo motor 455. At decision step 928, a determination is made whether another bag needs to be supplied for a next prescription order. If so, the method resumes at step 904. If no more prescription orders are to be processed, then the process ends. The above steps and/or sequence of steps may be modified as well, in accordance with the processes described herein.

In general, it should be emphasized that the various components of embodiments of the present invention can be implemented in hardware, software or a combination thereof. In such embodiments, the various components and steps would be implemented in hardware and/or software to perform the functions of embodiments of the present invention. Any presently available or future developed computer software language and/or hardware components can be employed in such embodiments of the present invention. For example, at least some of the functionality mentioned above could be implemented using Visual Basic, C, C++, or any assembly language appropriate in view of the processor(s) being used. It could also be written in an interpretive environment such as Java and transported to multiple destinations to various users.

The many features and advantages of embodiments of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system that places a label on a bag, comprising;
a first plurality of rollers contacting a bag film comprising a plurality of bags, each of the bags delimited by a perforation, said first plurality of rollers defining an area through which the bag film is conveyed, and rotating in concert in a first direction to convey the bag film, at least one of said plurality of rollers being driven to convey the bag film;
a printer for printing a plurality of labels, each label containing information corresponding to a particular order, disposed on a backing material;
a second plurality of rollers contacting the plurality of labels and the backing material, said second plurality of rollers defining an area through which the plurality of labels and the backing material are conveyed, and rotating in concert to convey the plurality of labels and the backing material for indicia to be printed thereon; and a label removal and tamp mechanism that receives at least one printed label containing information corresponding to the particular order, selectively removes the printed label containing information corresponding to the particular order from the backing material, and places the printed label on the bag.

2. The system according to claim 1, further comprising a first sensor for determining a first position of the bag, wherein said tamp places the printed label on the bag responsive to the hat position determined by said first sensor.

3. The system according to claim 1, further comprising:
at least one bag opening mechanism movably mounted to open the bag subsequent to labeling; and
a seal bar assembly comprising a heater element and a seal bar to seal the bag.

4. The system according to claim 3, wherein said at least one bag opening mechanism comprises a second sensor to determine whether the bag is in position for opening.

5. The system according to claim 3, further comprising a third sensor for detecting a position of perforation between the bag and a second bag.

6. The system according to claim 5, wherein the perforation position is used to convey the bag a predetermined amount in the first direction to said seal bar assembly.

7. The system according to claim 3, wherein said seal bar moves toward the bag to seal the bag.

8. The system according to claim 3, wherein at least a portion of said first plurality of rollers rotates in a second direction subsequent to sealing the bag to break a perforation between the bag and a second bag.

9. The system according to claim 3, wherein while a first bag is being tamped, a second bag is substantially simultaneously being opened by said at least one bag opening mechanism.

10. The system according to claim 1, further comprising a third roller that separates at least one of the plurality of labels from the backing material when the backing material rotates about said third roller.

11. The system according to claim 10, wherein a surface of said tamp comprises a plurality of vacuum holes that facilitate maintaining the label on the surface prior to placing the printed label on the bag.

12. The system according to claim 1, wherein at surface of said tamp comprises a plurality of vacuum holes that facilitate maintaining the label on the surface prior to placing the printed label on the bag.

13. The system according to claim 1, wherein at least one of said second plurality of rollers is under a biasing force and moves dynamically as labels are received by said printer.

14. The system according to claim 13, further comprising a spring, said spring providing the biasing force.

15. The system according to claim 13, further comprising a cam that moves in concert with the at least one of said second plurality of rollers under the biasing force.

16. The system according to claim 13, further comprising a switch that is engaged by said cam, wherein one of said second plurality of rollers comprises a label roll, and wherein when said switch is engaged by said cam, labels are dispensed from said label roll.

17. The system according to claim 1, further comprising a motor and a belt that drive the at least one of said first plurality of rollers.

18. The system according to claim 1, further comprising a controller that associates at least one of a pharmaceutical container and a literature package corresponding to a prescription order with to bag label.

19. The system according to claim 18, further comprising a robotic mechanism that places the pharmaceutical container in the bag.

20. A system that places a label on a bag, comprising:
a first dancer assembly that receives and conveys a bag film comprising a plurality of bags, each of the bags separated by a perforation, said first dancer assembly defining an area through which the bags are conveyed;
a printer for printing a plurality of labels, each label containing information corresponding a particular prescription order, disposed on a backing material;
a second dancer assembly that conveys the plurality of labels and the backing material, said second dancer assembly defining an area through which the plurality of labels and the backing material are conveyed;
a tamp that receives at least one printed label;
a control system that associates at least one of a pharmaceutical container and a literature package corresponding to the particular prescription order with the label corresponding to the particular prescription order; and
a sensor system disposed to sense a first position of the bag with respect to said tamp to facilitate said tamp placing the printed label corresponding to the prescription order on the bag responsive to the first position determined by said sensor system.

21. The system according to claim 20, further comprising:
at least one bag opening mechanism movably mounted to open the bag subsequent to labeling; and
a seal bar assembly comprising a heater element and a seal bar to seal the bag.

22. The system according to claim 21, wherein said at least one bag opening mechanism comprises a first sensor to determine whether a bag is in position for opening.

23. The system according to claim 21, further comprising a second sensor for detecting a position of a perforation between the bag and a second bag.

24. The system according to claim 23, wherein the perforation position is used to convey the bag a predetermined amount in a first direction to said seal bar assembly.

25. The system according to claim 23, wherein said seal bar moves toward the bag to seal the bag.

26. The system according to claim 21, wherein at least a portion of said first dancer assembly rotates in a second direction subsequent to sealing the bag to break a perforation between the bag and a second bag.

27. The system according to claim 20, further comprising a roller that facilitates selective removal of printed labels from the backing material when the backing material rotates about the roller.

28. The system according to claim 27, wherein a surface of said tamp comprises a plurality of vacuum holes that facilitate maintaining the label on the surface prior to placing the printed label on the bag.

29. The system according to claim 20, wherein a surface of said tamp comprises a plurality of vacuum holes that facilitate maintaining the label on the surface prior to placing the printed label on the bag.

30. The system according to claim 20, wherein said second dancer assembly comprises a roller under a biasing force, said roller moving dynamically as labels are received by said printer.

31. The system according to claim 30, further comprising a spring, wherein said spring provides the biasing force.

32. The system according to claim 30, further comprising a cam that moves in concert with the roller under the biasing force.

33. The system according to claim 32, further comprising:
a switch that is engaged by said cam; and
a label roll, wherein when said switch is engaged by said cam, labels are dispensed from said label roll.

34. The system according to claim 32, wherein at least a portion of said second dancer assembly comprises said label roll.

35. The system according to claim 20, wherein said first dancer assembly comprises a plurality of rollers.

36. The system according to claim 35, further comprising a motor and belt that drive at least one of said plurality of rollers.

37. A method for filling a plurality of prescription order, comprising the steps of:
transporting in a first direction a bag film comprising a plurality of bags;
transporting in the first direction a plurality of labels disposed on a backing sheet;
printing on a label for each of to plurality of bags, the name and address information of a recipient of a prescription order;
placing a label on the plurality of bags from the bag film, one bag at a time, when the plurality of bags reach a predetermined position;
opening the labeled bags; and
placing in the opened bag a pharmaceutical container with enclosed pharmaceuticals, corresponding to a prescription order associated with the bag label.

38. The method according to claim 37, further comprising to step of discarding a bag that cannot be opened.

39. The method according to claim 37, further comprising the step of placing a literature pack in the opened bag.

40. The method according to claim 39, further comprising the step of sealing the opened bag.

41. The method according to claim 40, further comprising the step of transporting the bag film in a second direction subsequent to sealing the bag to break a perforation between the sealed bag and a second bag.

42. The method according to claim 37, further comprising the step of sealing the opened bag.

43. The method according to claim 37, further comprising the step of conveying the bag a predetermined amount in the first direction to a position where the bag is opened, responsive to a perforation between a first bag and a second bag.

44. The method according to claim 43, further comprising the step of sensing whether a bag is in position for opening.

45. The method according to claim 37, further comprising the step sensing whether a bag is in position for opening.

46. The method according to claim 37, further comprising the step of separating a label from the backing sheet prior to said placing step.

47. The method according to claim 46, further comprising the step of providing a vacuum to hold the label in place prior to placing the label on at least one of the plurality of bags.

48. The method according to claim 37, further comprising the step of providing a vacuum to hold a label in place prior to placing the label on the plurality of bags.

49. The method according to claim 37, further comprising the step of placing a label on a first bag substantially simultaneously while opening a second bag having a label placed thereon.

50. A system that places a label on a bag, comprising:
means for contacting a bag film comprising a plurality of bags, each of to bags delimited by a perforation, said contacting means defining an area through which the bag film is conveyed, and rotating in concert in a first direction to convey the bag film, at least a portion of said contacting means being driven to convey to bag film;
a printer for printing a plurality of labels, each label containing information corresponding to a particular order, disposed on a backing material;
means for contacting the plurality of labels and the backing material, said label contacting means defining an area through which the plurality of labels and the backing material are conveyed, at least a portion of said label contacting means rotating in concert to convey the plurality of labels and the backing material for indicia to be printed thereon; and
a label removal and tamp mechanism that receives at least one printed label, selectively removes the printed label from the backing material and places the printed label on the bag corresponding to the particular order.

51. A system that places a label on a bag, comprising:
means for receiving and conveying a bag film comprising a plurality of bags, each of the bags separated by a perforation, said receiving and conveying means defining an area through which the bags are conveyed;
a printer for printing a plurality of labels, each label containing information corresponding to a particular prescription order, disposed on a backing material;
label conveying means for conveying the plurality of labels and the backing material, said label conveying means defining an area through which the plurality of labels and the backing material are conveyed;
a tamp that receives at least one printed label;
a control system that associates at least one of a pharmaceutical container and a literature package corresponding to the particular prescription order with the label corresponding to the particular prescription order; and
a sensor system disposed to sense a first position of the bag with respect to said tamp to facilitate said tamp placing the printed label corresponding to the particular prescription order on the bag responsive to the first position determined by said sensor system.

52. A system that places a label on a bag, comprising:
an order consolidation station configured to receive an order comprising a bottle from a first transport system and a package containing prepackaged pharmaceuticals from a second transport system;
a first plurality of rollers contacting a bag film comprising a plurality of bags, each of the bags delimited by a perforation, said first plurality of rollers defining an area through which the bag film is conveyed, and used to convey the bag film, at least one of said plurality of rollers being driven to convey the bag film;
a printer for printing a plurality of labels, each label containing information corresponding to a particular order, disposed on a backing material;
a second plurality of rollers contacting the plurality of labels and the backing material, said second plurality of rollers defining an area through which the plurality of labels and the backing material are conveyed, and used to convey the plurality of labels and the backing material for indicia to be printed thereon;

a label removal and tamp mechanism that receives at least one printed label containing information corresponding to the particular order, selectively removes the printed label containing information corresponding to the particular order from the backing material, and places the printed label on the bag; and at least one bag opening mechanism comprising at least one sensor to determine whether the bag is in position for opening to receive the order in cooperation with said order consolidation station.

53. The system according to claim 52, further comprising a control system that coordinates at least the order consolidation station and the at least one bag opening mechanism so that the order are placed into the bag when at least one identification information associated with the order and at least one other identifier information associated with the order correspond to the order.

* * * * *